(12) United States Patent
Bott et al.

(10) Patent No.: US 7,223,386 B2
(45) Date of Patent: May 29, 2007

(54) PREPARATIONS FOR TOPICAL SKIN USE AND TREATMENT

(75) Inventors: Richard R. Bott, Burlingame, CA (US); Mark S. Gebert, Pacifica, CA (US); Paal Christian Klykken, Midland, MI (US); Isabelle Mazeaud, Chatellerault (FR); Xavier Jean-Paul Thomas, Midland, MI (US)

(73) Assignees: Dow Corning Corporation, Midland, MI (US); Genencor International, Inc., Palo Alto, CA (US)

( * ) Notice: Subject to any disclaimer, the term of this patent is extended or adjusted under 35 U.S.C. 154(b) by 302 days.

(21) Appl. No.: 10/660,101

(22) Filed: Sep. 10, 2003

(65) Prior Publication Data
US 2004/0105874 A1    Jun. 3, 2004

Related U.S. Application Data

(63) Continuation-in-part of application No. 10/385,213, filed on Mar. 10, 2003.

(60) Provisional application No. 60/439,862, filed on Jan. 14, 2003, provisional application No. 60/363,386, filed on Mar. 11, 2002.

(51) Int. Cl.
*A61K 31/74*    (2006.01)
*A61K 38/46*    (2006.01)
*A61K 9/107*    (2006.01)
*C12N 9/00*    (2006.01)

(52) U.S. Cl. .................. 424/78.06; 424/400; 424/409; 424/484; 424/94.6; 435/183; 435/195; 524/267

(58) Field of Classification Search ..................... None
See application file for complete search history.

(56) References Cited

U.S. PATENT DOCUMENTS

| | | | |
|---|---|---|---|
| 2,736,721 A | 2/1956 | Dexter | |
| 2,814,601 A | 11/1957 | Currie et al. | |
| 2,857,356 A | 10/1958 | Goodwin, Jr. | |
| 3,528,940 A | 9/1970 | Modic | |
| 4,053,580 A | 10/1977 | Chien et al. | |
| 4,963,491 A | 10/1990 | Hellgren et al. | |
| 4,991,574 A | 2/1991 | Pocknell | |
| 5,010,115 A | 4/1991 | Grisoni | |
| 5,145,937 A | 9/1992 | Hergenrother et al. | |
| 5,153,135 A | 10/1992 | Farin et al. | |
| 5,232,702 A * | 8/1993 | Pfister et al. | ............... 424/448 |
| 5,306,498 A | 4/1994 | Fodor et al. | |
| RE34,606 E | 5/1994 | Estell et al. | |
| 5,389,536 A | 2/1995 | Gray et al. | |
| 5,605,694 A | 2/1997 | Bernard et al. | |
| 5,700,676 A | 12/1997 | Bott et al. | |
| 5,972,682 A | 10/1999 | Bott et al. | |
| 6,060,546 A * | 5/2000 | Powell et al. | ............... 524/267 |
| 6,153,205 A | 11/2000 | Boussouira et al. | |
| 6,168,782 B1 | 1/2001 | Lin et al. | |
| 6,177,071 B1 | 1/2001 | Lin et al. | |
| 6,200,581 B1 | 3/2001 | Lin et al. | |
| 6,207,717 B1 | 3/2001 | Lin et al. | |
| 6,238,657 B1 | 5/2001 | Lin et al. | |
| 6,328,983 B1 | 12/2001 | Afriat | |
| 6,337,086 B1 | 1/2002 | Kanios et al. | |
| 6,482,628 B1 | 11/2002 | Poulose et al. | |

FOREIGN PATENT DOCUMENTS

| | | |
|---|---|---|
| EP | 0 281 236 A | 9/1988 |
| EP | 0 425 164 A1 | 5/1991 |
| EP | 0 506 241 A1 | 9/1992 |
| EP | 0 955 347 A2 | 11/1999 |
| EP | 0 966 972 A1 | 12/1999 |
| FR | 2 686 510 A | 7/1993 |
| GB | 1 372 034 | 10/1974 |
| WO | WO 95/04537 A | 2/1995 |
| WO | WO 01/22923 A2 | 4/2000 |
| WO | WO 01/19190 A1 | 3/2001 |
| WO | WO 02/064103 A | 8/2002 |
| WO | WO 03/082230 A | 10/2003 |
| WO | WO 03/101404 A | 12/2003 |

* cited by examiner

*Primary Examiner*—Irene Marx
*Assistant Examiner*—Lora E Barnhart
(74) *Attorney, Agent, or Firm*—Dinsmore & Shohl LLP

(57) ABSTRACT

Topical preparations for release of an active agent and to methods of making and using the topical preparations are provided. The preparations may have an internal phase dispersed within an external phase. The internal phase may be a hydrophilic carrier and an active agent. The external phase may be a silicone matrix.

25 Claims, 13 Drawing Sheets

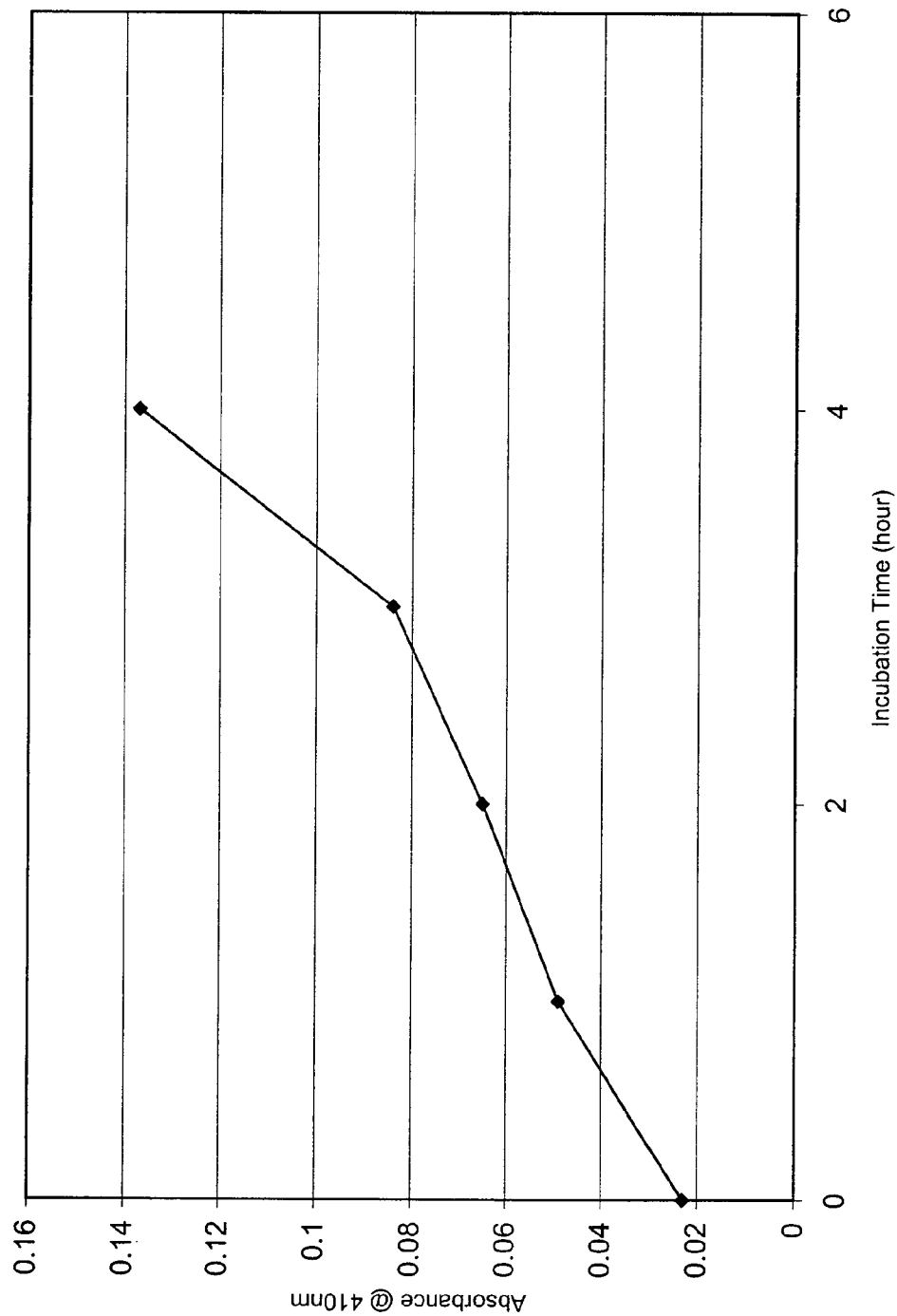

PREPARATIONS FOR TOPICAL SKIN USE AND TREATMENT

CROSS REFERENCES TO RELATED APPLICATIONS

The present application is a continuation-in-part of U.S. patent application Ser. No. 10/385,213, filed Mar. 10, 2003, which claims priority to U.S. Provisional Patent Application Ser. No. 60/363,386, filed Mar. 11, 2002 and U.S. Provisional Patent Application Ser. No. 60/439,862, filed Jan. 14, 2003.

BACKGROUND OF THE INVENTION

The present invention relates in general to preparations for topical skin treatment and, more particularly, to preparations comprising silicone matrices and hydrophilic carriers that provide sustained release of active agents.

Silicones are compounds based on alkylsiloxane or organosiloxane chemistry and include polydimethylsiloxane materials that have been used as excipients and process aids in pharmaceutical applications. Some of these materials have attained the status of pharmacopoeial compounds. Known in the art is the use of such silicone compounds in controlled drug delivery systems, especially in applications where the association of specific properties is critical to meet the requirements of product design, i.e., biocompatibility and versatility. New long lasting drug delivery applications including implant, insert, mucoadhesive, transdermal, and topical forms draw on the unique and intrinsic properties of silicone. These delivery systems allow controlled release of active molecules with biologically appropriate kinetics to a targeted area, and prevent the adverse effects, such as peak dosages, low compliance, and drug degradation, commonly observed with traditional oral and parenteral medication.

Transdermal drug delivery systems consist of drug containing adhesive patches, which adhere to intact skin up to 7 days. The patch design controls the release of the active agent, which is then carried through the organism by the circulatory system for a systemic activity. Using the skin as an entry point, the topical forms, which consist of an adhesive plaster or a film-forming and substantive material (e.g., cream or gel), are used for local treatment (muscle or skin disease). However, these transdermal drug delivery systems have not been incorporated into topical dressing applications such as wound dressings and ointments, wherein a biochemical agent dispersed within a silicone matrix is released onto skin or a wound to accelerate healing.

Accordingly, the need remains in the relevant art for preparations that take advantage of the beneficial properties of silicone, and can provide sustained release of active agents.

SUMMARY OF THE INVENTION

The present invention meets that need by providing topical preparations comprising a silicone matrix, a hydrophilic carrier, and at least one active agent for release from the preparation. The active agents may be proteins, particularly enzymes such as hydrolases and glucose oxidase. The silicone matrix can comprise high Mw polydimethylsiloxanes, loosely or lightly cross-linked silicone elastomers, cross-linked silicone elastomers such as gels (fillerless elastomers), silica reinforced rubbers or foam, in which the cross-linking is achieved using addition and condensation cure systems, silicone pressure sensitive adhesives, and silicone-organic copolymers such as silicone polyamide. The preparations may be used to form dressings, ointments, and the like.

In accordance with one aspect of the present invention, the preparation may comprise a thin film dressing that can be applied over the skin, including damaged tissue. In accordance with another aspect of the present invention, the preparation comprises a patch dressing. In accordance with still another aspect of the present invention, the preparation comprises a spread-on bandage dressing. In accordance with another aspect of the present invention, the preparation comprises an ointment. The thin film, the patch, the spread-on bandage, and the ointment can all be applied to the skin, over a surgical incision, a wound, or other skin lesion, abrasion, scrape, scratch, or other damaged tissue. The preparations may be occlusive to liquids and are effective in blocking microorganisms that cause infection from the skin surface. In one embodiment, active agents, such as protease, can be released from the preparations at the site of a wound for enzymatic debridement, clotting formation and clot removal, as well as in situ peroxide and/or peracid generation to accelerate wound healing at different stages thereof.

In a preferred embodiment, the topical preparation comprises a mixture of a hydrophilic carrier containing an active agent that is dispersed throughout a silicone matrix. The mixture together with the silicone matrix forms the topical preparation of this embodiment of the present invention. The hydrophilic carrier is, for example, a solution of propylene glycol, which may be mixed with a water soluble or hydrophilic component such as, for example, polyvinyl alcohol ("PVA") or polyvinylpyrrolidone ("PVP"). The hydrophilic carrier and active agent mixture may form an internal phase that is an emulsion or dispersion, and this internal phase is disposed within the silicone matrix (external phase). Consequently, a silicone-based surfactant can be added to disperse or emulsify the internal phase into very small droplets and enhance the release of active agent.

Accordingly, it is a feature of the present invention to provide topical preparations that are effective in providing controlled release of active agents to the skin. This and other features and advantages of the present invention will become apparent from the following detailed description of the invention.

BRIEF DESCRIPTION OF THE SEVERAL VIEWS OF THE DRAWINGS

The following detailed description of the preferred embodiments of the present invention can be best understood when read in conjunction with the following drawings in which:

FIGS. 2A and 2B are charts showing the release/delivery of protease and lipase from a preparation in accordance with an embodiment of the present invention.

DETAILED DESCRIPTION OF THE PREFERRED EMBODIMENTS

Figure 1:
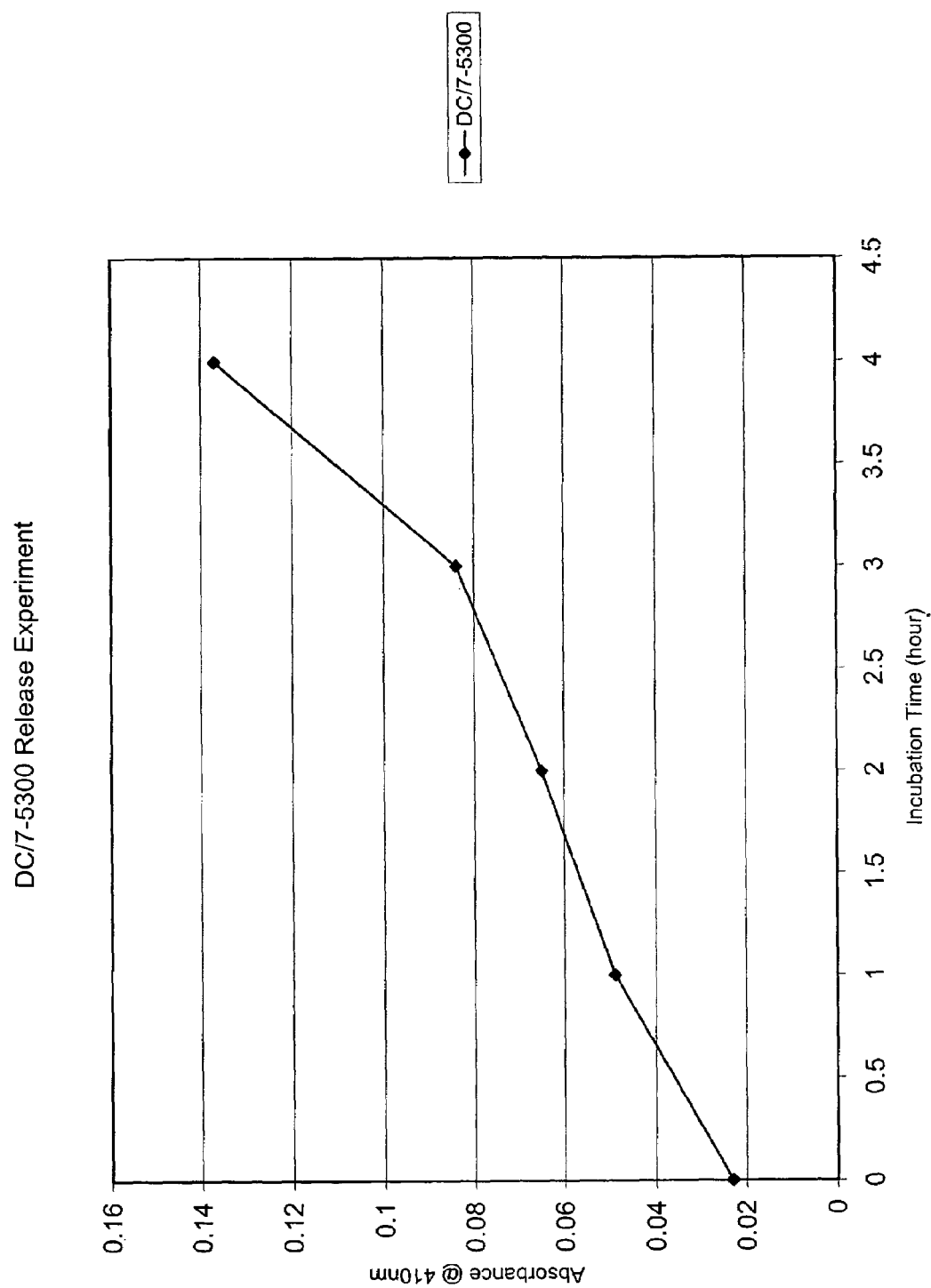
FIG. 1 is a chart of the sustained release of protease from a preparation in accordance with an embodiment of the present invention.

In accordance with one aspect of the present invention, a topical preparation incorporating a silicone matrix is provided. The preparation effectively provides controlled and sustained release of active agents from the silicone matrix. The active agents are blended with a hydrophilic carrier to form a mixture that is dispersed within the silicone matrix. The active agents remain stable within the silicone matrix and are controllably and freely released from the matrix.

For purposes of defining and describing embodiments of the present invention, the following terms will be understood as being accorded the definitions presented hereinafter.

Active Agent shall be understood as referring to proteins, and in particular to enzymes.

Surfactant shall be understood as referring to a surface-active agent added to a suspending medium to promote uniform and maximum separation of immiscible liquids or liquids and extremely fine solid particles, often of colloidal size. Surfactants promote wetting, efficient distribution of immiscible liquids, droplets, or fine solid particles in a liquid dispersing medium and stabilization against particle aggregation. The surfactant is generally added in the dispersing medium in amount sufficient to provide complete surface coverage of the particle surface.

Dressing shall be understood as referring to any of the various types of coverings that are suitable for application directly to skin, wounded tissue, or diseased tissue for absorption of secretions, protection of the tissue from trauma, administration of medication to the tissue, protection of the tissue from the environment, to stop bleeding, to maintain or provide a moist environment, and combinations thereof. For example, the dressing may be in the form of films, patches, bandages, gels and the like.

Emulsion shall be understood as referring to a temporary or permanent dispersion of one liquid phase within a second liquid phase. Generally one of the liquids is water or an aqueous solution, and the other is an oil or other water-immiscible liquid. The second liquid is generally referred to as the continuous or external phase. Emulsions can be further classified as either simple emulsions, wherein the dispersed liquid or internal phase is a simple homogeneous liquid, or a more complex emulsion, wherein the dispersed liquid phase is a heterogeneous combination of liquid or solid phases, such as a double emulsion or a multiple-emulsion.

Hydrophilic carrier shall be understood as referring to at least one component of a phase of the preparations of the present invention that acts as the solvent for the active agents. The hydrophilic carrier aids in the release of the active agent from the silicone matrices used in embodiments of the present invention.

Hydrophilic component shall be understood as referring to at least one component added to the mixture of the hydrophilic carrier and active agent in embodiments of the present invention. The hydrophilic component may aid in the release of the active agent from the silicone matrices used in embodiments of the present invention.

Protein shall be understood as referring to natural, synthetic, and engineered enzymes such as oxidoreductases, transferases, isomerases, ligases, hydrolases; antibodies; polypeptides; peptides; hormones; cytokines; growth factors; and other biological modulators.

Ointment shall be understood as referring to any suitable semisolid preparation for external application, such as to skin, wounded tissue, and diseased tissue.

In accordance with the present invention, the preparation may be used in a variety of topical dressings that may be applied to skin, wounded tissue, and diseased tissue. The topical dressings allow the active agents to be released and applied to the underlying skin, wounded tissue, and diseased tissue. Additionally, the preparation may be used to form ointments, and the ointments allow the active agents to be released and applied to the underlying skin, wounded, or diseased tissue.

In accordance with a preferred embodiment, a preparation is provided comprising an internal or non-miscible dispersed phase within an external or continuous phase. The external phase generally comprises a silicone matrix, and the internal phase generally comprises a hydrophilic carrier containing at least one active agent. Additionally, the internal phase may further comprise any suitable hydrophilic component. The internal and external phase may be mixed in any suitable manner to form the preparations of the present invention. For example, a high-shear mixer can be used to mix the internal and external phases in the formation of the preparations of the present invention. Additionally, the internal and external phases may be mixed by hand. The droplet size of the internal phase may vary. For example, the droplet size may be from about 0.1 µm up to about 2000 µm, from about 0.1 µm up to about 1000 µm, from about 0.1 µm up to about 500 µm, from about 0.1 µm up to about 200 µm, or from about 0.1 µm up to about 100 µm.

The internal phase may comprise any suitable hydrophilic carrier containing at least one active agent. In an embodiment according to the invention, the hydrophilic carrier is a liquid at relevant temperatures, and solid materials (for example sorbitol, manitol, lactose, sodium chloride and citric acid) dissolved in suitable solvent also may be used. For example, the active agent may be contained in a solution of propylene glycol (PPG), polyethylene glycol, poloxamer, glycerin, alcohol, polyhydric alcohol, water, or other suitable hydrophilic carrier.

The internal phase may further comprise a water soluble and hydrophilic component. The hydrophilic component generally does not serve as a solvent for the active agent. The hydrophilic component may enhance the release rate of the active agent from the silicone matrix and can include polyvinyl alcohol (PVA or PVOH) (such as, for example, Mowiol® 3-83 available from Clariant Corporation, Charlotte, N.C.) or polyvinylpyrrolidone (PVP), such as, for example, Luviskol® K-30 available from BASF Corporation, Mount Olive, N.J. The internal phase solution can include up to about 35 wt. % PVA solution in water or up to about 50 wt. % PVP solution in water. In an embodiment according to the invention, the hydrophilic component can also be a water-thickening agent diluted in water such as cellulosic derivatives (such as carboxymethylcellulose, methylcellulose, sodium carboxymethyl cellulose, hydroxypropylcellulose, hydroxypropylmethylcellulose), polyacrylic acids, alginate derivatives, chitosan derivatives, gelatin, pectin, polyethylene glycol, propylene glycol, glycerol and other suitable hydrophilic molecules and macromolecules in which the active agent may or may not be soluble. Such molecules include hydrophilic macromolecules.

While not wishing to be bound by any particular theory, it is contemplated that the hydrophilic components may create pores, crevices, cracks, or fissures within the silicone matrix, which facilitate the release of the active agent. The addition of increasing amounts of PVA or PVP to the hydrophilic carrier in creating the internal phase may increase the percentage of active agent that is released. In addition, increasing the amount of the hydrophilic carrier in the internal phase may increase the percentage of active agent that is released.

Additionally, excipients can be employed to stabilize or compatibilize the active agents, as well as assist in their release from the silicone matrix. Silicone excipients for use with the present invention can include silicone polyethers, silicone fluids, dimethicones, dimethicone copolyols, dimethiconols, silicone alkyl waxes, silicone polyamides and the like. Other possible excipients include, but are not limited to, hydrophilic organics such as (poly)saccharide derivatives, acrylate derivatives, PVA derivatives, glycol, glycerol, glyceride derivatives, propylene glycol (PPG), polyethylene glycol, poloxamer, glycerin, alcohol, cellulosic derivatives, polyacrylic acids, alginate derivatives, chitosan derivatives, gelatin, pectin and polyhydric alcohol.

The silicone matrix of the present invention may be comprised of high molecular weight polydimethylsiloxanes (12,500 cSt to gum-type material), such as those described in EP 966972 A1, WO 01/19190 A1, and WO 200122923, the disclosures of which are incorporated herein by reference for their teaching of high molecular weight polydimethylsiloxanes for use with the present invention.

The silicone matrix may be comprised of loosely or lightly cross-linked silicone elastomers, for example, Dow Corning® 9040 SILICONE ELASTOMER BLEND (available from Dow Corning Corporation, Midland, Mich.). Loosely or lightly cross-linked silicone elastomers are described in the following U.S. patents which describe loosely cross-linked polydimethylsiloxanes disposed in a volatile silicone solvent (D5), the disclosures of which are hereby incorporated herein by reference: U.S. Pat. Nos. 6,200,581, 6,238,657, 6,177,071, 6,168,782, and 6,207,717. As the volatile silicone solvent evaporates, the lightly or loosely cross-linked silicone elastomer thickens from a paste-like consistency to an elastomeric silicone gel.

The silicone matrix may also be comprised of fillerless elastomers, such as those described in U.S. Pat. Nos. 5,145,937 and 4,991,574, and EP 0955347, which are hereby incorporated herein by reference for their teaching of silicone gels for use with the present invention, for example, Dow Corning® 7-9800 SSA KIT (available from Dow Corning Corporation, Midland, Mich.).

The silicone matrix may alternatively be comprised of a cellular elastomer (fillerless or reinforced with silica), such as those described in EP 0425164, EP 0506241, and U.S. Pat. No. 5,010,115, the disclosures of which are hereby incorporated herein by reference for their teaching of silicone foams for use with the present invention for example, Dow Corning® 7-0192 FOAM PART A and PART B (available from Dow Corning Corporation, Midland, Mich.). Further, the silicone matrix can be comprised of a silicone rubber, such as an addition cure (similar to a gel, but reinforced with silica) or a condensation cure, for example, Dow Corning® 7-5300 FILM-IN-PLACE COATING or Dow Corning® 7-FC4210 FILM FORMING BASE AND CURE AGENT (available from Dow Corning Corporation, Midland, Mich.).

Finally, the silicone matrix may be comprised of a silicone pressure sensitive adhesive (silicone PSA), such as a silicate resin in silicone polymers, which can be solvent based or hot-melt, such as those described in U.S. Pat. Nos. 2,736,721, 2,814,601, 2,857,356, 3,528,940, and 6,337,086, the disclosures of which are hereby incorporated herein by reference for their teaching of silicone PSAs for use with the present invention. For example, Dow Corning® PSA 7-4402 (available from Dow Corning Corporation, Midland, Mich.) may be used.

The silicone matrix of the present invention may further comprise a silicone-based surfactant, for example, Dow Corning® 9011 SILICONE ELASTOMER BLEND (available from Dow Corning Corporation, Midland, Mich.) that facilitates the dispersion or emulsification of the hydrophilic carrier and active agent into small droplets and prevents these smaller droplets from coalescing into larger droplets. For example, the droplets of the internal phase may be from about 0.1–500 µm when a silicone based surfactant is employed. The silicone-based surfactant may also be employed to produce a stable emulsion in the formation of the topical dressings of the present invention. In addition, the external phase of the present invention may include a diluent for delivering the silicone matrix, such as a volatile silicone (i.e., D5 (Dow Corning® 245 fluid), and MDM (Dow Corning® 200 fluid 1 cSt)), or an organic solvent (i.e., heptane or ethyl acetate).

The active agents of the present invention are generally proteins, such as enzymes, that are incorporated into the hydrophilic carrier. The active agents may be hydrophilic. Enzymes suitable for incorporation in the dressing may be any enzyme or enzymes. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases and mixtures thereof.

Lipase enzymes which may be considered to be suitable for inclusion in the preparations of the present invention include those produced by microorganisms of the *Pseudomonas* group, such as *Pseudomonas stutzeri* ATCC 19.154, as disclosed in British Patent 1,372,034; *Pseudomonas mendocina*, as described in U.S. Pat. No. 5,389,536, and *Pseudomonas pseudoalcaligenes*, as disclosed in U.S. Pat. No. 5,153,135. Lipases further include those that show a positive immunological cross-reaction with the antibody of the lipase, produced by the microorganism *Pseudomonas fluorescens* IAM 1057. This lipase is available from Amano Pharmaceutical Co. Ltd., Nagoya, Japan, under the trade name Lipase P "Amano". Lipases include M1 Lipase® and Lipomax® (Gist-Brocades NV, Delft, Netherlands) and Lipolase® (Novozymes A/S, Bagsvaerd, Denmark). The lipases are normally incorporated in the silicone matrix at levels from about 0.0001% to about 2% of active enzyme by weight of the silicone matrix, or from about 0.001 mg/g to about 20 mg/g.

Proteases are carbonyl hydrolases which generally act to cleave peptide bonds of proteins or peptides. As used herein, "protease" means a naturally-occurring protease or a recombinant protease. Naturally-occurring proteases include alpha.-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

The protease can be of animal, plant, or microorganism origin. For example, the protease may be a serine proteolytic enzyme of bacterial origin. Purified or nonpurified forms of enzyme may be used. Protease enzymes produced by chemically or genetically modified mutants are included by definition, as are close structural enzyme variants. Particularly preferred by way of protease enzyme is bacterial serine proteolytic enzyme obtained from Bacillus, particularly subtilases, for example *Bacillus subtilis, Bacillus lentus, Bacillus amyloliquefaciens*, and/or *Bacillus licheniformis*. Suitable commercial proteolytic enzymes which may be considered for inclusion in the present invention compositions include Alcalase®, Esperase®, Durazym®, Everlase®, Kannase®, Relase®, Savinase®, Maxatase®, Maxacal®, and Maxapem® 15 (protein engineered Maxacal); Purafect®, Properase® (protein engineered Purafect) and subtilisin BPN and BPN'.

Protease enzymes also encompass protease variants having an amino acid sequence not found in nature, which is derived from a precursor protease by substituting a different amino acid sequence not found in nature, which is derived from a precursor protease by substituting a different amino acid for the amino acid residue at a position in said protease equivalent to positions equivalent to those selected from the group consisting of +76, +87, +99, +101, +103, +104, +107, +123, +27, +105, +109, +126, +128, +135, +156, +166, +195, +197, +204, +206, +210, +216, +217, +218, +222, +260, +265, and/or +274 according to the numbering of *Bacillus amyloliquefaciens* subtilisin, as described in U.S. Pat. No. RE 34,606; U.S. Pat. Nos. 5,700,676; 5,972,682 and/or 6,482,628, which are incorporated herein by reference in their entirety.

Exemplary protease variants include a subtilisin variant derived from *Bacillus lentus*, as described in U.S. Pat. No. RE 34,606, hereinafter referred to as Protease A. Another suitable protease is a Y217L variant derived from *Bacillus amyloliquesfaciens*, as described in U.S. Pat. No. 5,700,676, hereinafter referred to as Protease B. Also suitable are what are called herein Protease C, which is a modified bacterial serine proteolytic enzyme described in U.S. Pat. No. 6,482,628; and Protease D, which is a modified bacterial serine proteolytic enzyme described in U.S. Pat. No. 5,972,682. Also suitable is LG12 a *B. subtilis* protease as described in U.S. Pat. No. 5,677,163, which is incorporated by reference herein.

Other proteases useful in the practice of this invention can be selected from the group consisting of Savinase®, Esperase®, Maxacal®, Purafect®, BPN', Protease A, Protease B, Protease C, Protease D and mixtures thereof. Protease enzymes are generally present in the preparations of the present invention at levels from about 0.01% to about 0.5% by weight of the silicone matrix, or from about 0.1 mg/g to about 10.0 mg/g, and preferably from about 0.1 mg/g to about 5.0 mg/g.

It will be understood by those having skill in the art that the present invention is not limited to the enzymes listed above. It shall be further understood by those having skill in the art that one or more active agents can be utilized in the topical preparations of the present invention.

The active agents may perform a variety of functions. For example, the matrix can release proteases and other enzymatic debriding agents topically for removal of necrotic tissues and general wound cleansing, clotting formation and clot removal enzymes, agents which generate peroxide, peracid, activated oxygen species, and anti-adhesion catalytic antagonists for self-sterilization, anti-infection, and acceleration of healing, and agents for skin treatment and the like.

The preparations in accordance with the present invention may have any suitable amounts of the components. For example, the external phase may comprise about 50.000% to about 99.999% of the topical preparation. The internal phase may comprise about 0.001% to about 2.000% active agent and about 0.001% to about 49.999% hydrophilic carrier. When a surfactant is added to the preparation, the surfactant may comprise about 0.001% to about 60.000%, more generally about 0.100% to about 50.000%. When a hydrophilic component is added, the hydrophilic component may comprise about 0.001% to about 50.000% of the preparation, and the hydrophilic component may more generally comprise about 5.000% to about 40.000% of the topical preparation. In another embodiment, the hydrophilic component may comprise about 10.000% to about 35.000% of the preparation. In yet another embodiment, the hydrophilic component may comprise about 15.000% to about 35.000% of the preparation.

A preparation In accordance with the present invention may be created by preparing the internal phase by mixing a hydrophilic carrier solution, such as a propylene glycol solution, containing the active agent together with a hydrophilic component solution on a rotating mixer at about 30 rpm for about 15 minutes. The ingredients of the external phase, such as a silicone matrix and silicone-based surfactant, are pre-mixed to obtain a homogeneous mixture.

After both the internal and external phases are individually prepared, the mechanical operation of emulsification or dispersion can be carried out. Preferably, the internal phase is added to the external phase and vigorously stirred with a high shear laboratory mixer, i.e., a Silverson L4R with a square hole high shear screen (available from Silverson Machines, Inc., East Longmeadow, Mass.). Such high shear mixing results in droplets having diameters of between about 0.1 and 50 µm, about 0.1 and 10 µm, and about 0.1 and 5 µm with very narrow size distribution. Stirring of the mixture can be carried out at about 5400 rpm for about 90 seconds. The resultant mixture may then be transferred to a suitable container to cure. The container can be sized and/or shaped to provide a desired patch.

Alternatively, the dressings can be prepared by hand mixing. In accordance with another embodiment of the present invention, the internal and external phases are prepared as described above, and the internal phase is added to the external phase. The mixture is then vigorously stirred for about 30 seconds in a container by applying circular motion with a small spatula to form the dressings. Hand mixing of the internal and external phases may result in internal phase droplets having diameters between about 10 and about 1000 µm.

The preparations of the present invention may be cast into a film prior to application to the skin or applied to the skin directly where they polymerize in situ. A "spread-on" film polymerizes when applied to the skin and may be delivered as a cream or ointment from a tube, sachet, roll-on, spray, patch, bandage and the like in accordance with the present invention. The film can be created by incorporating a silicone rubber, such as an addition cure (similar to a gel, but reinforced with silica) or a condensation cure, for example, Dow Corning® 7-5300 FILM-IN-PLACE COATING available from Dow Corning Corporation (Midland, Mich.), into the external phase. Upon mixing with the internal phase, the resultant emulsion is allowed to cure and provides a "spread-on" film, patch, or bandage, which polymerizes when applied to the skin and effectively releases an active agent such as protease. The emulsion may be spread onto a substrate to achieve a desired thickness. It will be understood by those having skill in the art that the dressings of the present invention may be prepared by any suitable method and that the preparation methods are not limited to those described herein.

An ointment in accordance with the present invention may be created stirring together a silicone elastomer, such as Dow Corning® 9041 SILICONE ELASTOMER BLEND, and a silicone surfactant, such as Dow Corning® 5200 FORMULATION AID available from Dow Corning Corporation (Midland, Mich.), to form the external phase. The internal phase may be prepared by mixing together an active agent solution and a hydrophilic carrier such as PVA. The internal phase may be incorporated into the external phase by adding the internal phase to the external phase slowly with constant stirring.

It shall be understood by those having skill in the art that the preparations of the present invention may be prepared to optimize the release rate of the active agent for a given application. For example, the silicone matrix may be selected to provide an increased or decreased rate of active agent release. The rate of active agent release may be increased by the addition of hydrophilic components such as PVA and PVP to the silicone matrix. Similarly, adding increased amounts of a hydrophilic carrier may increase the rate of active agent release, for example, up to about 50% by weight of hydrophilic carrier may be used to form the preparations. Alternatively, the silicone matrix may be chosen to increase the rate of active agent release. For example, a silicone matrix having a low cross-link density will provide a faster active agent release rate than a silicone matrix having a high cross-link density.

The thickness of the dressing patch may also be changed to affect the active agent release rate. The thickness of the patch may be adjusted downwardly in order to increase the active agent release rate. Additionally, the dressing may be prepared to be more occlusive to air. As the occlusivity of the dressing increases, the release rate of the active agent may increase.

Similarly, the parameters of the wound bed may cause the active agent release rate to be increased or decreased. For example, as the amount of moisture in the wound bed increases, the active agent release rate may also increase. Alternatively, as the temperature of the wound bed increases, the active agent release rate may increase. Thus, the various parameters of the preparations may be chosen to optimally deliver the active agent at a desired release rate for a given set of wound bed and dressing or ointment conditions.

Generally, the preparations should be formulated to provide a dressing or ointment that may be stored for a given period of time without losing a significant proportion of its active agent activity. For example, the dressings or ointments may be stable at room temperature for a period of up to six months without losing more than an effective percentage of their activity.

As discussed above, the preparations may be prepared such that an active agent or agents is released from the silicone matrix that may remove necrotic tissues. The preparations may be occlusive to fluids, and this occlusivity may promote a moist wound environment in areas covered by the preparations. The moist wound environment may allow the swelling of necrotic tissues covered by the preparations, and this swelling may allow the active agents to more effectively and selectively remove the swollen necrotic tissues.

In accordance with one embodiment of the present invention, the area around a wound having necrotic tissues may have an adhesive applied thereon, and the adhesive may be used to adhere the preparations over the wound. The adhesive may comprise a silicone matrix comprising a silicone pressure sensitive adhesive as described herein such as Dow Corning® PSA 7-4402, a hydrophilic carrier such as PVA, and an active agent that is selected to inhibit the active agent selected to remove necrotic tissue so that the healthy tissue is protected. The active agent may be released from the adhesive as described herein. For example, if the active agent in the preparation over the wound comprises a protease, the active agent in the adhesive may be a protease inhibitor. Examples of suitable protease inhibitors include, but are not limited to, serine protease inhibitors such as those found in the serpin, Kunitz, Kazal, and leukoproteinase classes of inhibitors. Such suitable inhibitors are found in R. M. Roberts, et al., *Regulation and Regulatory Role of Proteinase Inhibitors*, Crit. Rev. Eukaryot. Gene Expr. 5 (3–4) 385–436 (1995).

In order that the invention may be more readily understood, reference is made to the following examples, which are intended to be illustrative of the invention, but are not intended to be limiting in scope.

EXAMPLE 1

A first experiment was conducted to evaluate the sustained release of protease from a silicone matrix. A loosely or lightly cross-linked silicone elastomer composition (Dow Corning® 9040) and a silicone-based surfactant (Dow Corning® 9011), both commercially available from Dow Corning Corporation (Midland, Mich.), were used to form a Dow Corning® 9040 and a Dow Corning® 9040/9011 silicone elastomer formulation. A 1.1 mg/ml protease A, derived from *B. lentus*, stock solution dissolved in propylene glycol was added to both Dow Corning® compositions. A 5 ml. sample of the stock solution was added to 20 grams of the 9040 formulation and also to 20 grams of the 9040/9011 formulation, which comprises 10 grams of the 9040 formulation and 10 grams of the 9011 formulation. Controls comprising 9040 and 9040/9011 plus water instead of the stock enzyme solution were prepared. In addition, to determine whether any component of the silicone matrix was inhibiting the protease, further samples were prepared having an equal amount of the Dow Corning® 9040 and 9040/9011 enzyme formulations, and the controls with water which were free of protease. These inhibition controls were prepared by taking aliquots from these protease-free samples and adding them to equal amounts of aliquots from the enzyme formulation samples to observe for inhibition of protease activity. The sample materials were then air dried in a hood for two weeks.

The Dow Corning®9040/9011 formulation dried to a thin film and the Dow Corning® 9040 composition dried in cakes. The samples were assayed using a standard assay for protease using N-succinyl-L-Ala-L-Ala-L-Pro-L-Phe-p-nitroanilide (SAAPFpNA) as described by Delmar, E. G., et al. (1979) Anal. Biochem. 94, 316–320; Achtstetter, Arch. Biochem. Biophys 207:445–54 (1981)) (pH 6.5, 25° C.). The assay measured released protease in units of mAbs/min at 410 nanometers using a Hewlett Packard 8451A Diode Assay Spectrophotometer. The results of this first example are shown in Table 1 below:

TABLE 1

Release of Protease

| | Time (hours) | | | |
|---|---|---|---|---|
| | 1 | 2 | 3 | 5 |
| 9040 + protease | 3.21 | 3.58 | 3.71 | 4.04 |
| 9040 (inhibition) | 2.95 | 3.24 | 3.33 | 4.04 |
| 9040/9011 + protease | 0.995 | 0.175 | 0.205 | 0.294 |
| 9040/9011 (inhibition) | 0.912 | 0.163 | 0.197 | 0.256 |
| 9040/water control | 0.000 | 0.000 | 0.000 | 0.000 |
| 9040/9011 water control | 0.000 | 0.000 | 0.000 | 0.000 |

* Expressed units are mAbs/min of released protease.

These data indicate the effective release of protease from the silicone matrix over a 5-hour period. The data is from material stored dry for more than two weeks. The controls of protease-free silicone formulations and the inhibition controls were incubated with the same volume and for the same duration as the silicone formulations containing protease. The inhibition samples show a fairly consistent value of protease activity lower than the protease activity of the enzyme formulations. The results indicate that some slightly inhibitory compound may be present when additional formulation is added to the enzyme sample.

EXAMPLE 2

Another experiment was conducted to evaluate the sustained release of protease from a silicone matrix. A 0.5 ml aliquot of 0.81 mg/ml Protease A in polyethylene glycol stock solution was transferred into a small polypropylene weighing boat. Next, 5.0 ml of a silicone rubber composition (Dow Corning® 7-5300 from Dow Corning Corporation, Midland, Mich.) was added to the protease solution and mixed within 15 seconds of its addition. It is contemplated that the Dow Corning® 7-5300 composition has applications as a "spread-on" film, patch, or bandage. The mixture was then allowed to cure for 30 minutes. Following curing, the mixture was washed three times using 1.0 ml of distilled water. Each wash was assayed using the SAAPFpNA assay on the aliquots, as referenced above, and the amount of enzyme in the wash was measured. The composition was then dried on its side for 15 minutes, followed by an additional 15 minutes laying flat. Finally, 5.0 ml of distilled water was added to the weigh boat and swirled gently for a few seconds. A 200 µl aliquot was taken for the zero time point. The weight boat was continually swirled, taking 200 µl for the hourly time points.

The results of this experiment are reported in FIG. 1. Nine percent (9%) protease activity was recovered in the washes and 3.8% protease was released from the silicone matrix in 4 hours.

The Dow Corning® 7-5300 silicone rubber composition was further examined for lipase release, using a lipase derived from *P. mendocina*, by the method described directly above. The results of this experiment in mAbs/min units are set out in Table 2 below:

TABLE 2

Lipase Release

| Time (h) | 0 | 1 | 2 | 3 | 6.5 | 9 |
|---|---|---|---|---|---|---|
| Lipase Activity | .0268 | .0264 | .0387 | .0476 | .0624 | .0787 |
| % total | .073 | .073 | 1.06 | 1.3 | 1.71 | 2.16 |

Eighteen percent (18%) lipase activity was recovered in the washes and 2.2% lipase was released in 9 hours.

Figure 2B:
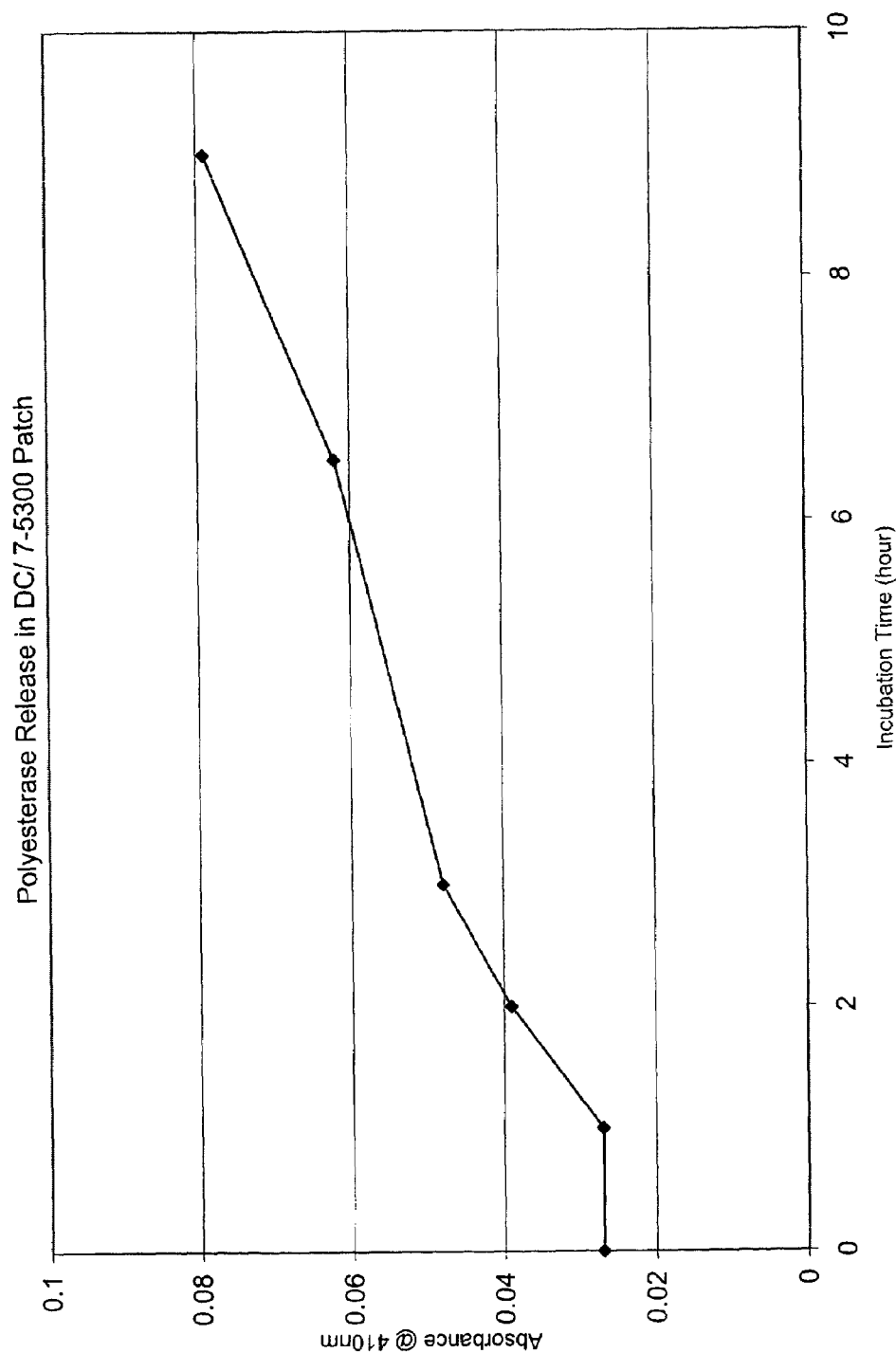

FIG. 2A illustrates the release/delivery of Protease A and FIG. 2B illustrates the release/delivery of lipase from the Dow Corning® 7-5300 silicone rubber solution. The figure indicates a linear release over time of ~2–4% of added enzyme from the silicone matrix.

EXAMPLE 3

Still another experiment was conducted to evaluate the effect of hydrophilic additives on the sustained release of Protease A from a silicone matrix. First, test dressings or, more specifically, patches containing protease were cast into small petri-dishes (approximately 3 cm in diameter) such that the total weight of the patches was constant (about 2 grams) and the concentration of enzyme in the patches was also constant (about 0.6 mg agent per gram of patch). The patches were comprised of a loosely or lightly cross-linked silicone elastomer composition (Dow Corning® 9040) and a silicone-based surfactant (Dow Corning® 9011), both commercially available from Dow Corning Corporation (Midland, Mich.). In addition, Dow Corning® 7-5300 (a silicone rubber composition) was also tested. Additionally, the formulations contained varying amounts of PVA, PVA at high propylene glycol levels, or PVP that were added by stirring.

Enzyme release was evaluated using two methods. In the first method, the patches were washed to remove any enzyme that may have been present on the surface of the patch and very close to the patch surface. About 1 ml of dissolution buffer (10 mM Tris, 10 mM CaCl$_2$, and 0.005% Tween 80 at pH 5.4) was added to the petri dish on top of the test patch. The buffer was then swirled for 20 seconds and the buffer was decanted into an Eppendorf tube for analysis. The wash step was repeated three (3) times and the enzyme activity was measured for each wash. The results were summed to give the total amount of enzyme released during the washing process. This amount of enzyme was included at the zero time point in FIGS. 3A–3C.

The alternative method does not include the washing step. About 5 ml of dissolution buffer was pipetted on top of the test patch and the petri dish was covered with a lid to eliminate evaporation. The petri dish containing the test patch and the dissolution buffer was then swirled at about 75 rpm on an elliptical mixer and 10 µl aliquots of dissolution buffer were removed at one hour increments for analysis of enzyme activity. The aliquots were pipetted directly into a cuvette containing assay buffer (100 mM Tris and 0.005% Tween 80 at pH 8.6) and the enzyme activity was measured on a UV/visible spectrometer, which gave the concentration of enzyme in the dissolution buffer in mg/ml.

Figure 3A:
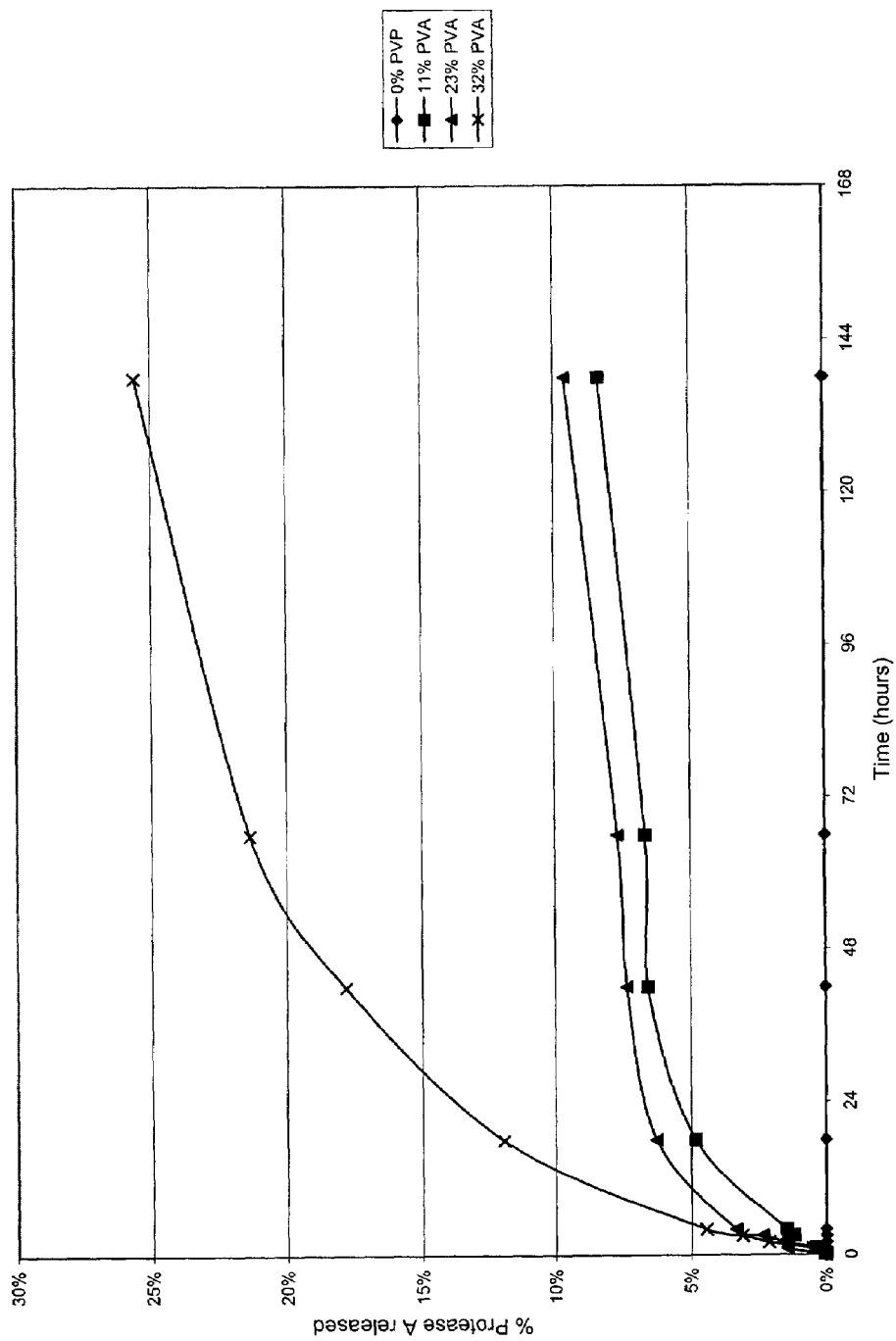
FIGS. 3A–3C are charts showing the release of proteases from preparations having varying amounts of hydrophilic components.
Figure 3B:
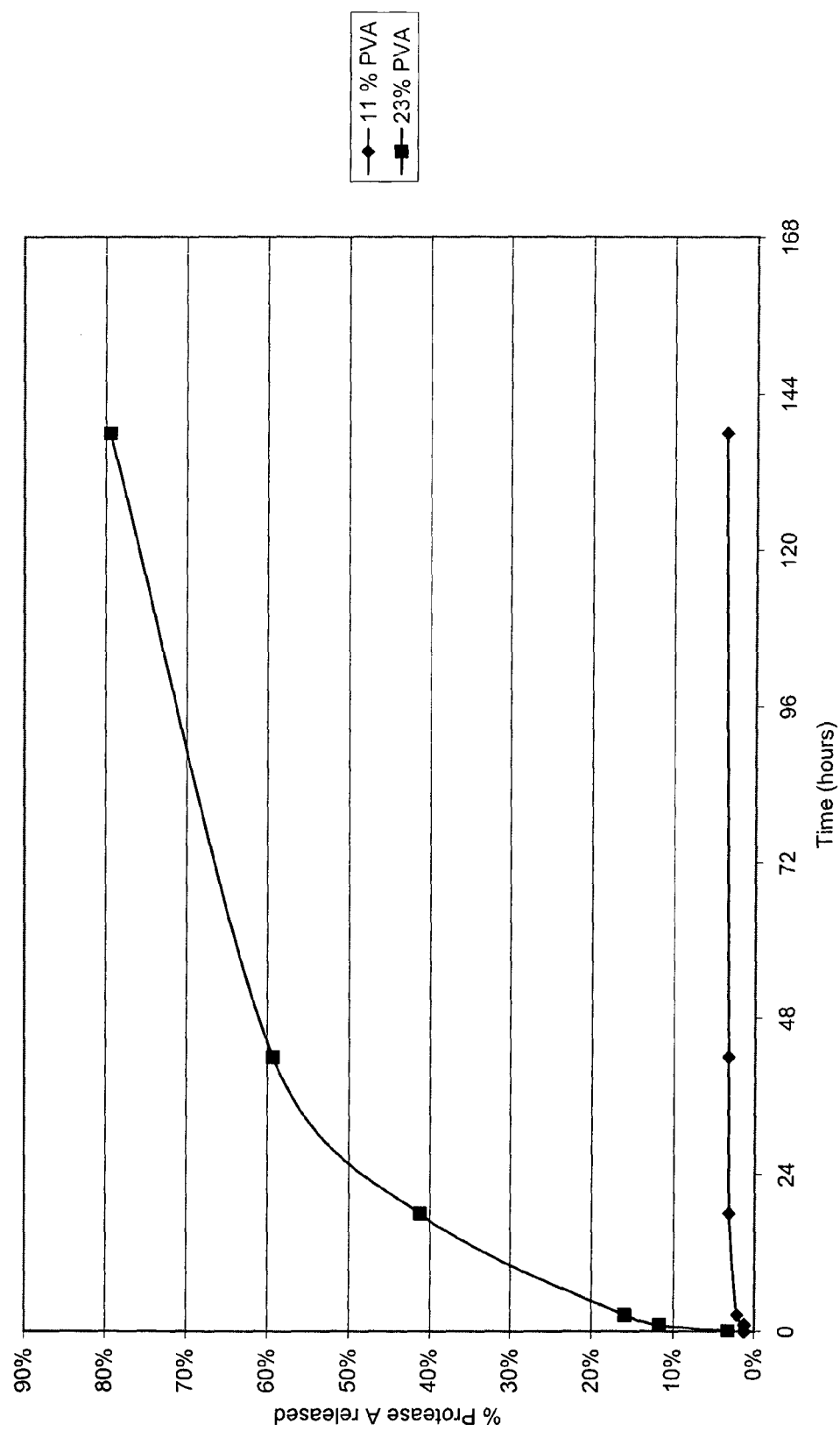
Figure 3C:
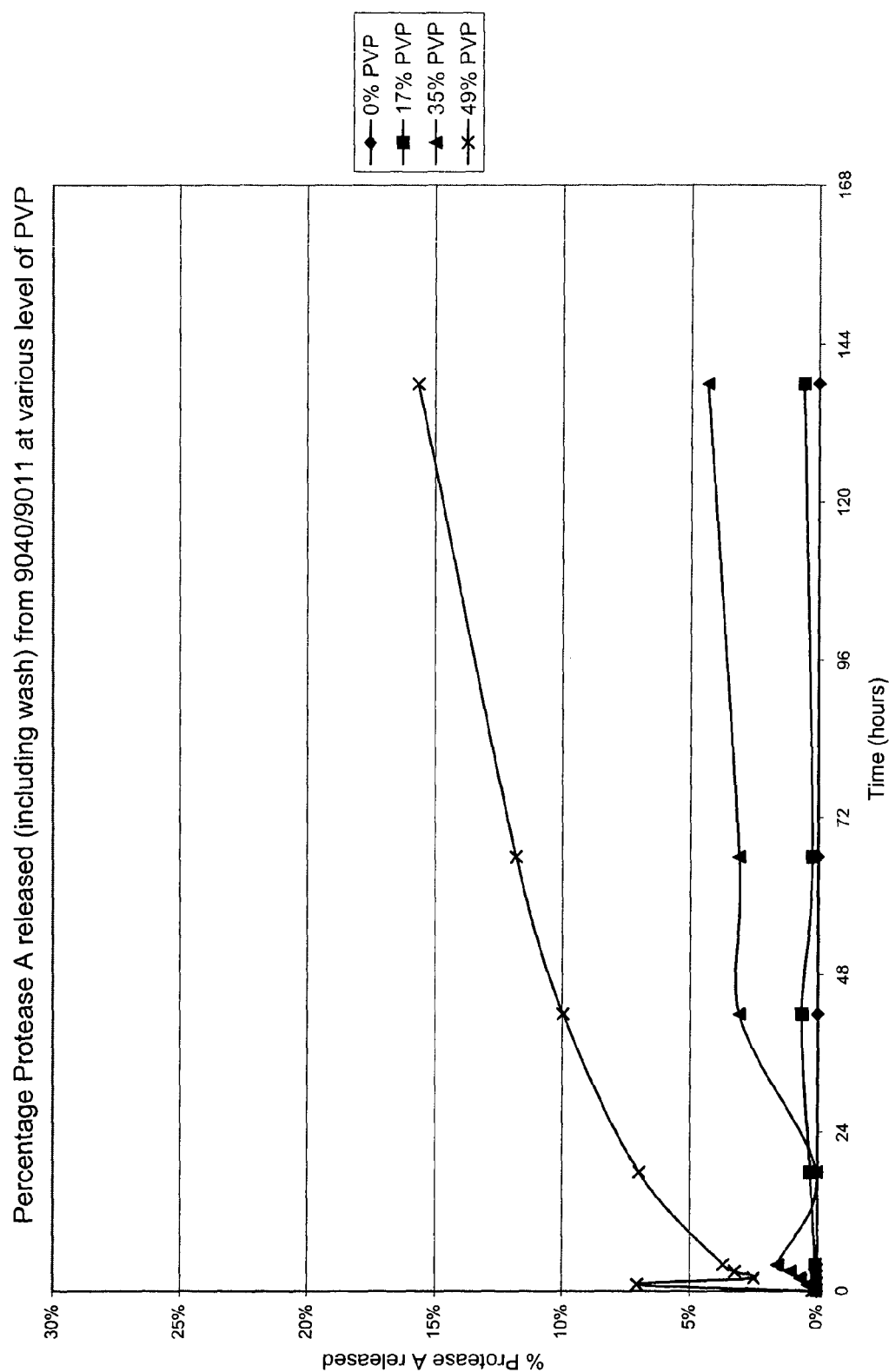

FIG. 3A illustrates the release of the enzyme with varying amounts of PVA and with a high PG (propylene glycol) content from the Dow Corning® 9040/9011 silicone matrix. As is seen in FIG. 3A, the addition of larger amounts of hydrophilic PVA to the silicone matrix increases the rate of release of the enzyme. Similarly, FIG. 3B illustrates the percentage of Protease A released from the Dow Corning® 7-5300 formulations at various levels of PVA. As can be seen from the graph, the rate of release increases as the amount of PVA increases. FIG. 3C illustrates the release of the enzyme from a Dow Corning® 9040/9011 silicone matrix with varying amounts of PVP. As is seen in FIG. 3C, the addition of hydrophilic PVP to the silicone matrix increases the rate of release of the enzyme.

EXAMPLE 4

An experiment was conducted to evaluate the effect of the silicone matrices on the sustained release of Protease B from a silicone matrix. First, test dressings or, more specifically, patches containing protease were cast into small petri-dishes (approximately 3 cm in diameter) such that the total weight of the patches was constant (about 2 grams) and the concentration of enzyme in the patches was also constant (about 0.6 mg agent per gram of patch). The patches were comprised of a loosely or lightly cross-linked silicone elastomer composition (Dow Corning® 9040) and a silicone-based surfactant (Dow Corning® 9011), both commercially available from Dow Corning Corporation (Midland, Mich.). Alternatively, the patches were comprised of Dow Corning® PSA 7-4402 a pressure sensitive adhesive or Dow Corning®7-FC-4210 a cellular elastomer both available from Dow Corning Corporation (Midland, Mich.). Additionally, the formulations contained 0% or 20% PVA.

Enzyme release was evaluated using two methods. In the first method, the patches were washed to remove any enzyme that may have been present on the surface of the patch and very close to the patch surface. About 1 ml of dissolution buffer (10 mM Tris, 10 mM $CaCl_2$, and 0.005% Tween 80 at pH 5.4) was added to the petri dish on top of the test patch. The buffer was then swirled for 20 seconds and the buffer was decanted into an Eppendorf tube for analysis. The wash step was repeated three (3) times and the enzyme activity was measured for each wash. The results are summed to give the total amount of enzyme released during the washing process. This amount of enzyme was included at the zero time point in FIG. 4.

The alternative method does not include the washing step. About 5 ml of dissolution buffer was pipetted on top of the test patch and the petri dish was covered with a lid to eliminate evaporation. The petri dish containing the test patch and the dissolution buffer was then swirled at about 75 rpm on an elliptical mixer and 10 µl aliquots of dissolution buffer were removed at one hour increments for analysis of enzyme activity. The aliquots were pipetted directly into a cuvette containing assay buffer (100 mM Tris and 0.005% Tween 80 at pH 8.6) and the enzyme activity was measured on a UV/Visible spectrometer, which gave the concentration of enzyme in the dissolution buffer in mg/ml.

Figure 4:
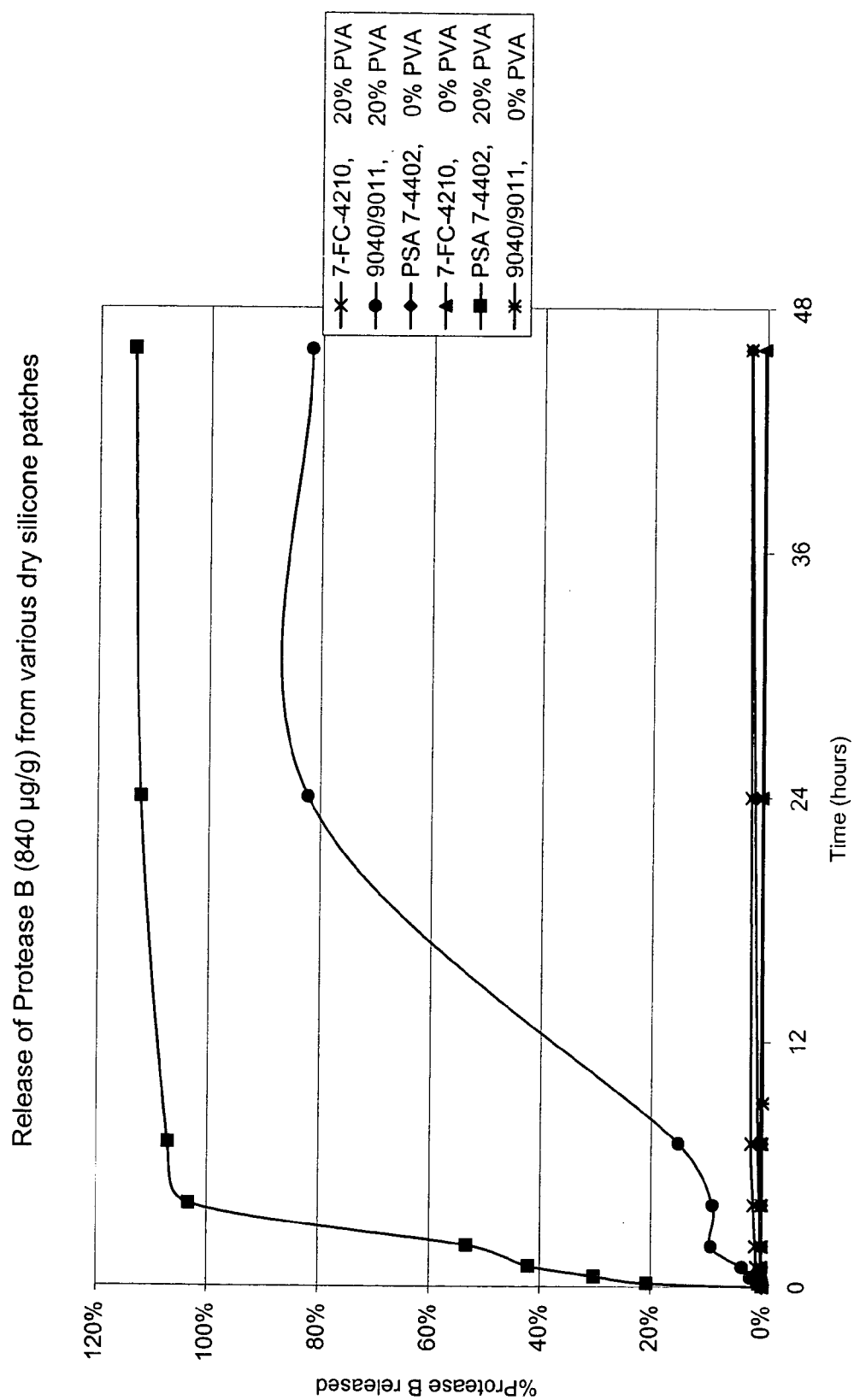
FIG. 4 is a chart showing the release rate of protease from preparations having varying silicone matrices.

FIG. 4 illustrates the results of this enzyme release study. As can be seen from the graph, the PSA 7-4402 matrix has the greatest release rate. The release rate of the enzyme is affected by the cross-link density of the silicone matrix.

EXAMPLE 5

An experiment was conducted to observe the effect of patch thickness on the rate of enzyme release. Test formulations containing Protease B, 7-5300 silicone, and other components such as PVA were emulsified. The formulations were spread onto a Mylar® sheet using a Blade Applicator (UV Process Supply, Inc., Chicago). The thickness of the applied coating was controlled by adjusting the gap between the blade and the Mylar® sheet. The coating was applied at 13 and 25 µm respectively. After the coating was allowed to dry or cure completely, 25 mm diameter test discs were cut from the Mylar® sheet. The final dry thickness of the coating was measured using a digital coating thickness gauge (Elcometer, Manchester, UK). The final dry weight of the test sample disks was also measured so that the enzyme payload was accurately known. The weight and thickness of the Mylar® alone was measured and subtracted from that of the samples on the Mylar® to yield the weight and thickness of the sample alone.

The enzyme release studies were performed using a Franz Diffusion Cell (Amie Systems, Riegelsville, Pa.). The test samples were mounted on the top of the diffusion cell and the cell was filled with 13.7 milliliters of dissolution buffer (10 mM MES with 10 mM NaCl and 0.005% Tween 80 at pH 5.5) that was preheated to 37° C. Care was taken to remove any air bubbles that were inside the diffusion cell. The stirring rate of the cell was preset to 50 rpms. Sample aliquots of 0.1 ml were withdrawn from the diffusion cell at regular time intervals and analyzed for enzyme activity to give an active enzyme concentration in units of mg/ml. The percentage of enzyme released was also calculated.

Figure 5:
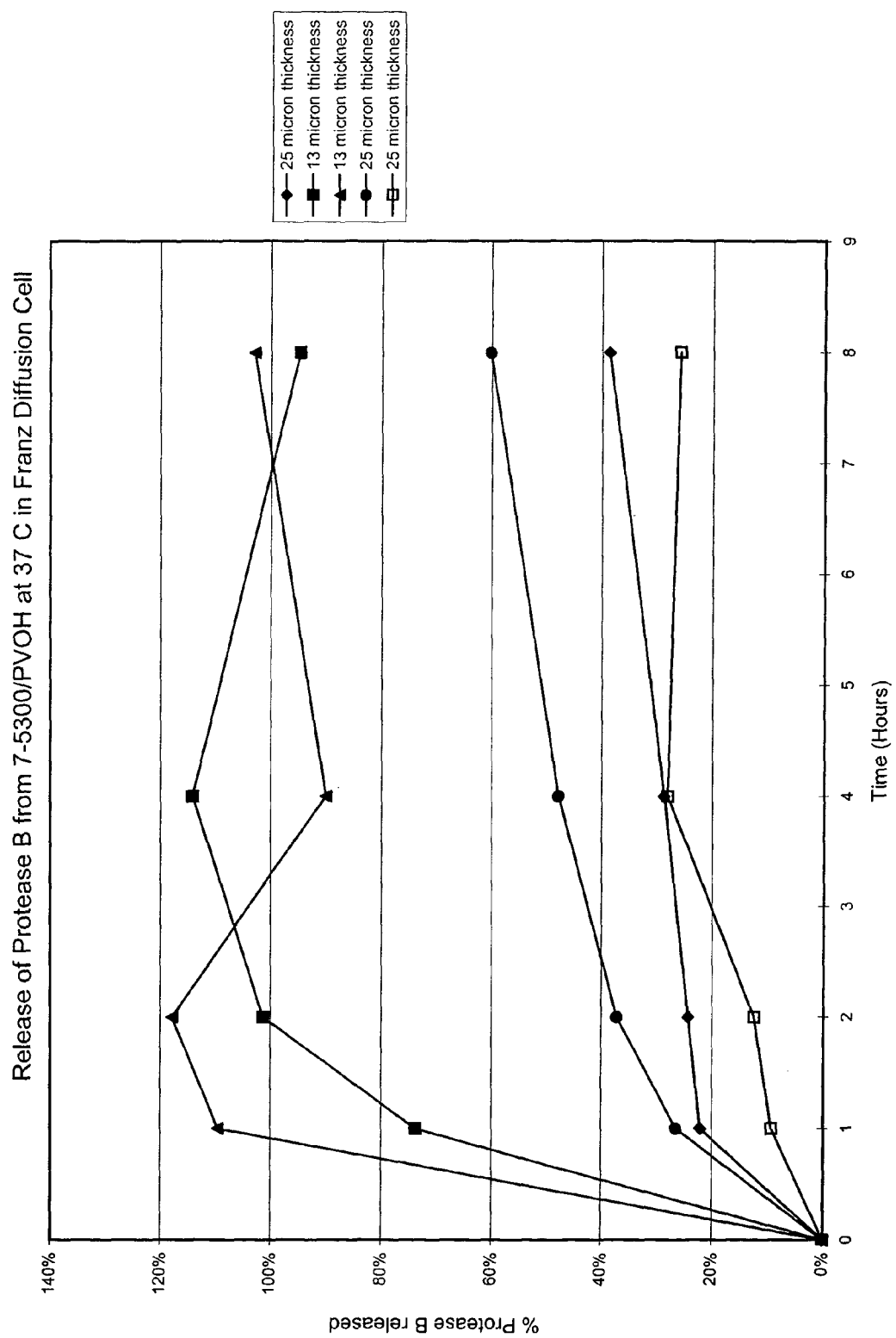
FIG. 5 is a chart showing the release rate of protease from preparations having a varying patch thickness.

As can be seen with reference to FIG. 5, the release rate was found to be inversely proportional to patch thickness. Therefore, 100% release of the enzyme was achieved from the thinnest patches.

EXAMPLE 6

An experiment was conducted to study the release of protease from an ointment formulation. Test ointment formulations were prepared by preparing an external phase containing a silicone elastomer Dow Corning 9041 and a silicone surfactant Dow Corning 5200 formulation aid both available from Dow Corning Corporation (Midland, Mich.). An internal phase was prepared containing Protease B stock solution. Additionally, the internal phase was prepared to have 0 or 20% of a 40% PVA solution. The Protease B stock solution contained active enzyme, sodium formate, calcium chloride, water, and PG. The internal and external phases were mixed using a mechanical stirrer. The ointment had about 3 milligrams of enzyme per gram of ointment.

After the ointment formulations were prepared, their release rate was measured using a Hansen Ointment Cell (Hansen, Chatworth, Calif.) to determine the stability of the formulations. Approximately 0.5 grams of ointment was loaded into the ointment cell in the ointment dose area. A 0.45 µm HT Tuffryn® Membrane (Pall Corp., Ann Arbor, Mich.) was placed on top of the ointment dose and the ointment cell was sealed closed. The ointment cell was then placed in the ointment cell flask and the flask was filled with 25 milliliters of pH 5.5 buffer solution (10 mM MES, 10 mM $CaCl_2$, 0.005% Tween), submersing the ointment cell in the buffer solution. The test was run at 30° C. and the buffer was stirred at a constant 50 rpms using a paddle. After 10 min, 1 hr, 2 hrs, 4 hrs, 8 hrs, 16 hrs and 24 hrs, a 0.5 ml aliquot is withdrawn via an autosampler. The enzyme activity is measured on a UV/Visible spectrometer to give the concentration of enzyme in the dissolution buffer in mg/ml. The dissolution test is done on 6 replicates and the average amount is reported.

Figure 6:
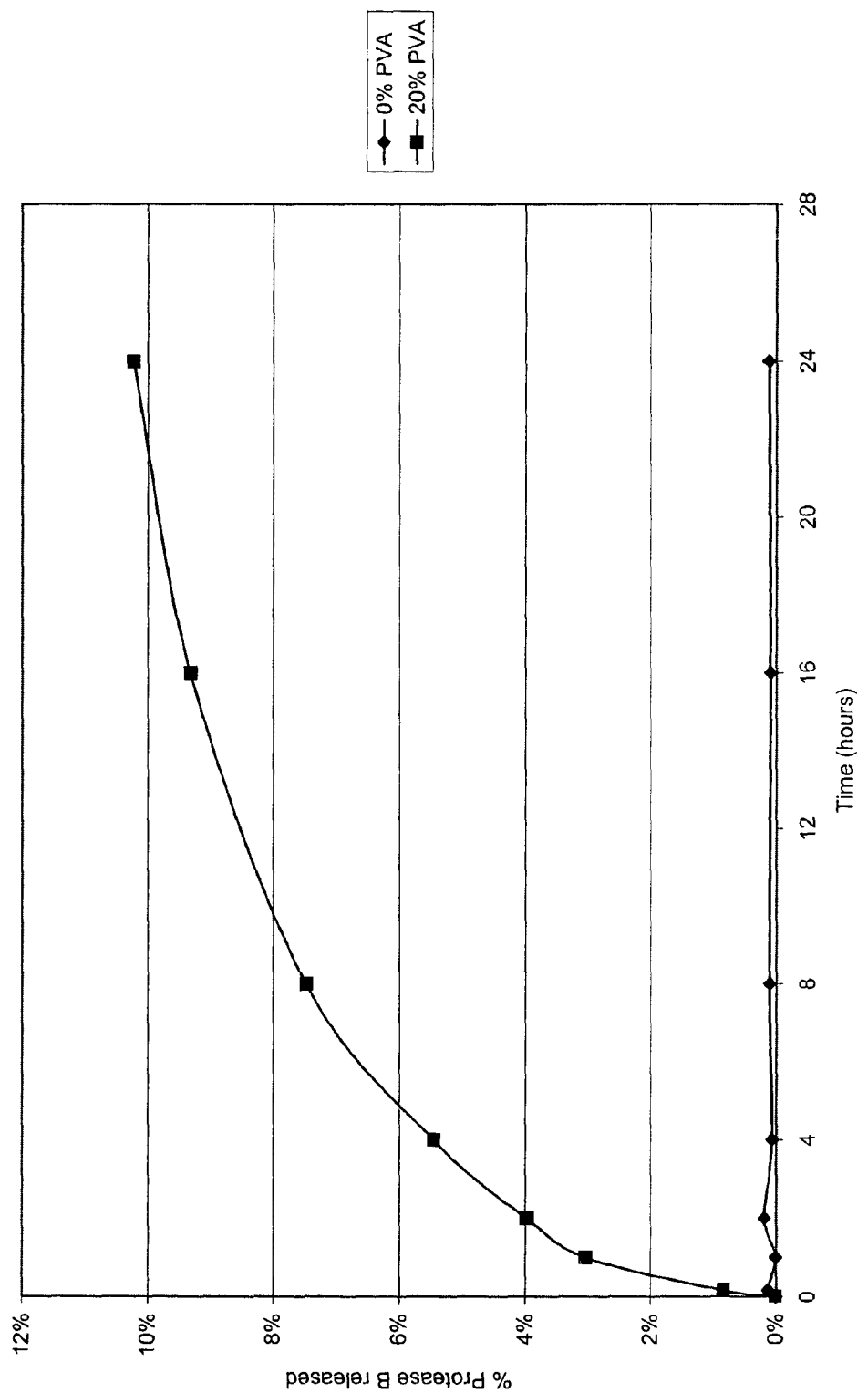
FIG. 6 is a chart showing the release of protease from an ointment formulation in accordance with an embodiment of the present invention.

Referring to FIG. 6, the addition of the PVA solution allows the enzyme to be partially released from the ointment over a period of 24 hours. It is apparent from FIG. 6 that the ointment provides a preparation that may be used to topically treat skin.

EXAMPLE 7

A stability study was performed to measure the stability of the enzyme within a dry patch stored at room temperature. Release of enzyme after storage comparable to the initial release data reported in the Examples above indicates that the enzyme remains stable during storage. The dry patches were stored for a period of time ranging from 0 to 6 months and the enzyme release was measured at the appropriate time points. Test formulations containing Protease A, 9040/9011 silicone and other components were emulsified. The test formulations comprised 3.1250 g dry weight of DC-9040 silicone, 3.2500 g dry weight DC-9011 silicone surfactant, 2.5 mg/g Protease A and 4.2000 g dry weight PVA. The formulations were spread onto a Mylar® sheet using a Blade Applicator (UV Process Supply, Inc., Chicago). The thickness of the applied coating was controlled by adjusting the gap between the blade and the Mylar® sheet. After the coating was allowed to dry or cure completely, 25 mm diameter test discs were cut from the Mylar® sheet. The final dry thickness of the coating was measured using a digital coating thickness gauge (Elcometer, Manchester, UK), and the samples were approximately 100 µm thick. The final dry weight of the test sample disks was also measured so that the enzyme payload is accurately known. The weight and thickness of the Mylar® alone was measured and subtracted from that of the samples on the Mylar® to yield the weight and thickness of the samples alone.

A control comprising Protease A stock solution (50% Sodium formate buffer containing 400 ppm calcium chloride at pH 5.5) in 50% propylene glycol was prepared. The control was stored at room temperature, and the enzymatic activity retained was tested at various time points. The Protease A enzyme is expected to be stable in the control solution.

The enzyme release studies were performed using a Hanson (Hanson, Chatsworth, Calif.) dissolution tester equipped with an auto sampling attachment and a small volume dissolution kit. The test samples were fastened to a 3/16" thick glass disc of the same diameter as the sample (25 mm) using rubber cement. The samples were then loaded into the dissolution vessels with the test sample side facing upward. 25 milliliters of dissolution buffer (10 mM MES with 10 mM NaCl and 0.005% Tween 80 at pH 5.5) was poured on top of each sample and the stirring paddles along with auto sampler tubes were immediately lowered into the buffer. The dissolution vessel was capped to minimize evaporation and the stirring was started at 50 rpm's. The auto sampler withdrew either a 0.5 ml or 1 ml aliquot at programmed time points and these samples were analyzed for enzyme activity using the SAAPFpNA protease assay referenced above to give an active enzyme concentration in mg/ml. In some cases, total protein was also determined at each time point by measuring the absorbance at 280 nm and applying the appropriate extinction coefficient.

Figure 7:
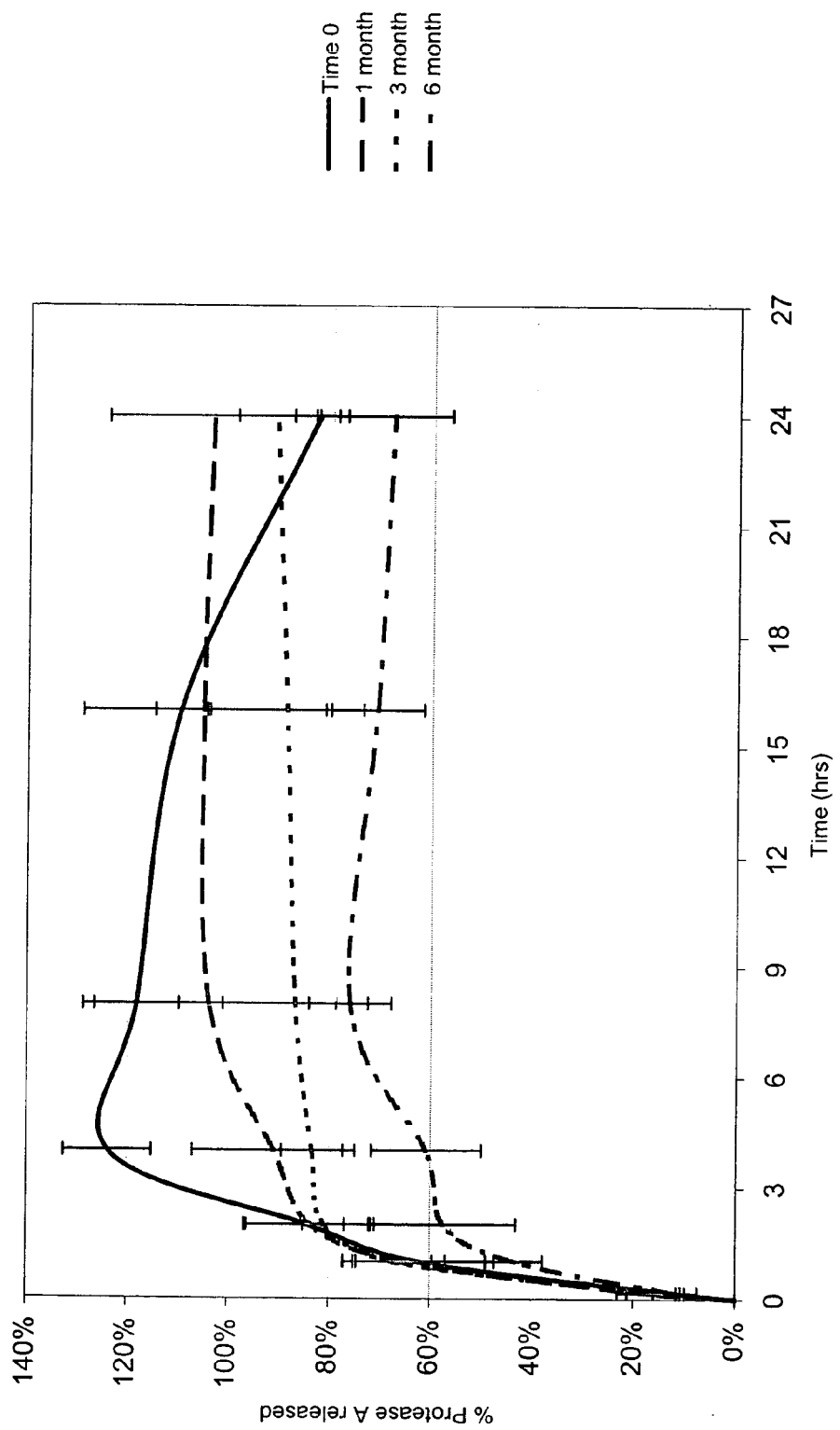
FIG. 7 is a chart showing the stability of protease in preparations in accordance with an embodiment of the present invention.

Referring to FIG. 7, the enzymatic stability of Protease A from a 9040/9011 dry patch stored for 0, 1, 3, and 6 months are illustrated. The data points are from an average of 6 replicates for each time point. The loss of activity is greater in the control solution than in the silicone patch. Therefore, the silicone patch provides a more stable means of storing and subsequently releasing the enzyme.

EXAMPLE 8

A stability study was performed to measure the stability of the enzyme within a dry patch having PSA 7-4402 stored at room temperature. Release of enzyme after storage comparable to the initial release data reported in the Examples above indicates that the enzyme remains stable during storage. The dry patches were stored for a period of time ranging from 0 to 6 months and the enzyme release was measured at the appropriate time points. Test formulations containing Protease B, PSA 7-4402 silicone and other components were emulsified. The test formulations comprised 33.7500 dry weight of PSA 7-4402 silicone, 2.3500 g dry weight of DC 193 fluid (available from Dow Corning Corp., Midland, Mich.), 3.8612 mg/g Protease B, and 9.4100 g dry weight PVA. The formulations were spread onto a Mylar® sheet using a Blade Applicator (UV Process Supply, inc., Chicago). The thickness of the applied coating was controlled by adjusting the gap between the blade and the Mylar® sheet. After the coating was allowed to dry or cure completely, 25 mm diameter test discs were cut from the Mylar® sheet. The final dry thickness of the coating was measured using a digital coating thickness gauge (Elcometer, Manchester, UK), and the samples were approximately 100 µm thick. The final dry weight of the test sample disks was also measured so that the enzyme payload is accurately known. The weight and thickness of the Mylar® alone was measured and subtracted from that of the samples on the Mylar® to yield the weight and thickness of the samples alone.

A control comprising Protease B stock solution (50% Sodium formate buffer containing 400 ppm calcium chloride at pH 5.5) in 50% propylene glycol was prepared. The control was stored at room temperature, and the enzymatic activity retained was tested at various time points. The Protease B enzyme is expected to be stable in the control solution.

The enzyme release studies were performed using a Hanson (Hanson, Chatsworth, Calif.) dissolution tester equipped with an auto sampling attachment and a small volume dissolution kit. The test samples were fastened to a 3/16" thick glass disc of the same diameter as the sample (25 mm) using rubber cement. The samples were then loaded into the dissolution vessels with the test sample side facing upward. 25 milliters of dissolution buffer (10 mM MES with 10 mM NaCl and 0.005% Tween 80 at pH 5.5) was poured on top of each sample and the stirring paddles along with auto sampler tubes were immediately lowered into the buffer. The dissolution vessel was capped to minimize evaporation and the stirring was started at 50 rpm's. The auto sampler withdrew either a 0.5 ml or 1 ml aliquot at programmed time points and these samples were analyzed for enzyme activity using the SAAPFpNA protease assay referenced above to give an active enzyme concentration in mg/ml. In some cases, total protein was also determined at each time point by measuring the absorbance at 280 nm and applying the appropriate extinction coefficient.

Figure 8:
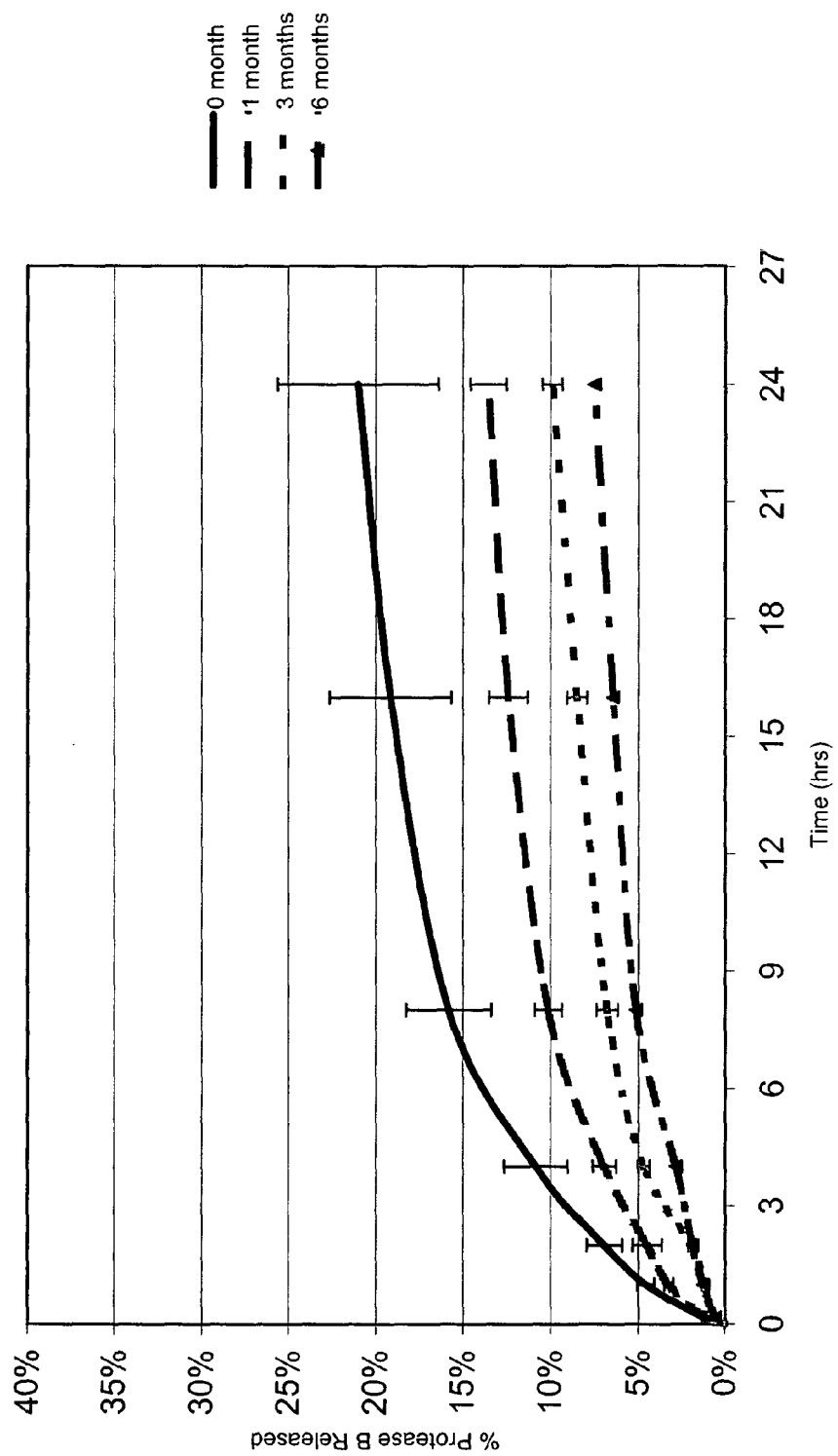
FIG. 8 is a chart showing the stability of protease in preparations in accordance with another embodiment of the present invention.

Referring to FIG. 8, the enzymatic stability of Protease B from a PSA 7-4402 dry patch stored for 0, 1, 3, and 6 months are illustrated. The data points are from an average of 6 replicates for each time point. The silicone patch provides a stable means of storing and subsequently releasing the enzyme. However, the percentage of Protease B released is less than the percentage of activity retained in the Protease B control solution.

EXAMPLE 9

A stability study was performed to measure the stability of the enzyme within a dry patch having PSA 7-4401 stored at room temperature. Release of enzyme after storage comparable to the initial release data reported in the Examples above indicates that the enzyme remains stable during storage. The dry patches were stored for a period of time ranging from 0 to 3 months and the enzyme release was measured at the appropriate time points. Test formulations containing Protease B, PSA 7-4401 silicone and other components were emulsified. The test formulations comprised 33.9088 dry weight of PSA 7-4401 silicone, 2.3500 g dry weight of DC 193 fluid, 3.8723 mg/g Protease B, and 9.6170 g dry weight PVA. The formulations were spread onto a Mylar® sheet using a Blade Applicator (UV Process Supply, Inc., Chicago). The thickness of the applied coating was controlled by adjusting the gap between the blade and the Mylar® sheet. After the coating was allowed to dry or cure completely, 25 mm diameter test discs were cut from the Mylar® sheet. The final dry thickness of the coating was measured using a digital coating thickness gauge (Elcometer, Manchester, UK), and the samples were approximately 100 µm thick. The final dry weight of the test sample disks was also measured so that the enzyme payload is accurately known. The weight and thickness of the Mylar® alone was measured and subtracted from that of the samples on the Mylar® to yield the weight and thickness of the samples alone.

A control comprising Protease B stock solution (50% Sodium formate buffer containing 400 ppm calcium chloride at pH 5.5) in 50% propylene glycol was prepared. The control was stored at room temperature, and the enzymatic activity retained was tested at various time points.

The enzyme release studies were performed using a Hanson (Hanson, Chatsworth, Calif.) dissolution tester equipped with an auto sampling attachment and a small volume dissolution kit. The test samples were fastened to a 3/16" thick glass disc of the same diameter as the sample (25 mm) using rubber cement. The samples were then loaded into the dissolution vessels with the test sample side facing upward. 25 milliters of dissolution buffer (10 mM MES with 10 mM NaCl and 0.005% Tween 80 at pH 5.5) was poured on top of each sample and the stirring paddles along with auto sampler tubes were immediately lowered into the buffer. The dissolution vessel was capped to minimize evaporation and the stirring was started at 50 rpm's. The auto sampler withdrew either a 0.5 ml or 1 ml aliquot at programmed time points and these samples were analyzed for enzyme activity using the SAAPFpNA protease assay referenced above to give an active enzyme concentration in mg/ml. In some cases, total protein was also determined at each time point by measuring the absorbance at 280 nm and applying the appropriate extinction coefficient.

Figure 9:
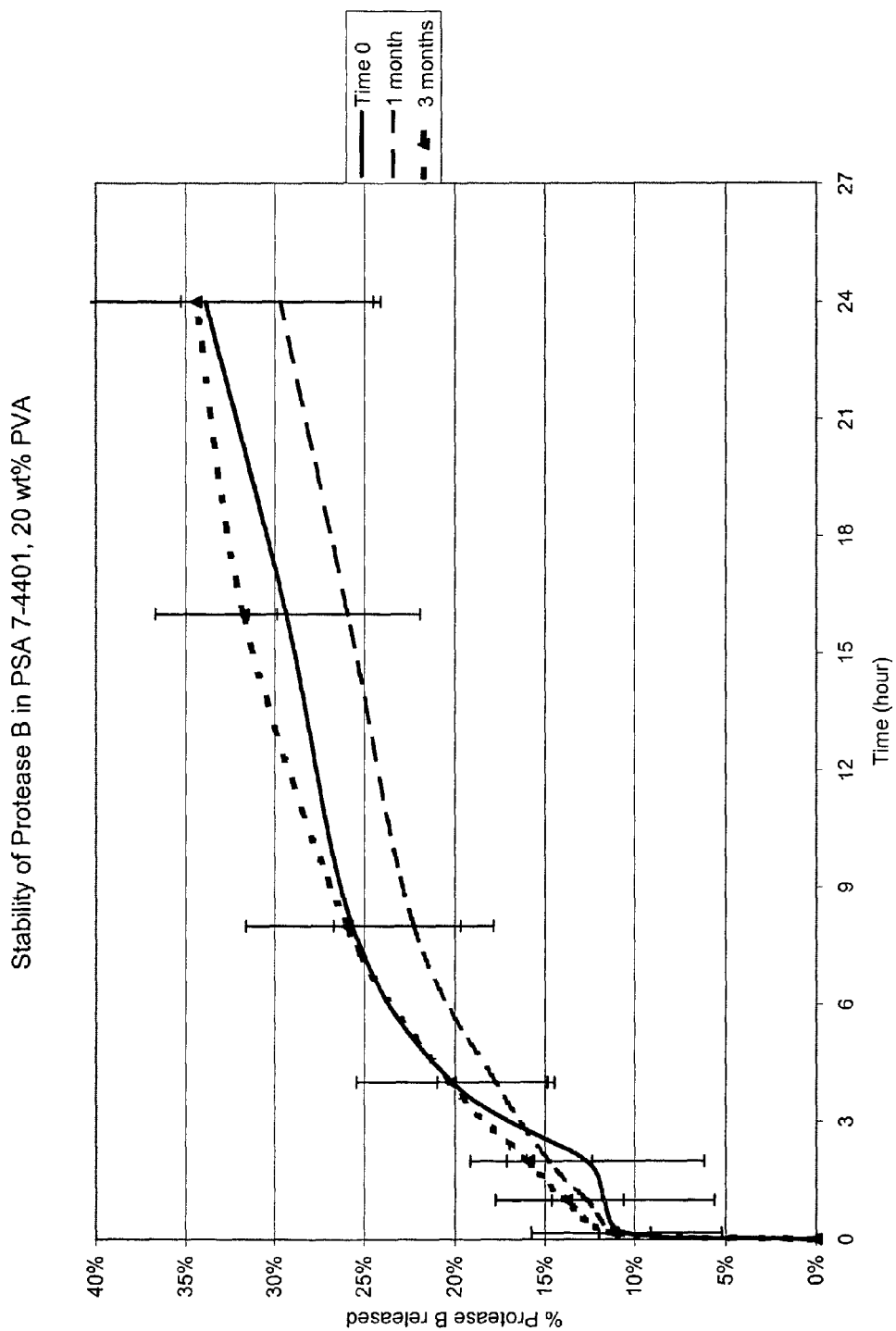
FIG. 9 is a chart showing the stability of protease in preparations in accordance with yet another embodiment of the present invention.

Referring to FIG. 9, the enzymatic stability of Protease B released from a PSA 7-4401 dry patch stored for 0, 1, and 3 months are illustrated. The data points are from an average of 6 replicates for each time point. The silicone patch provides a stable means of storing and subsequently releasing the enzyme. However, the percentage of Protease B released is less than the percentage of activity retained in the Protease B control solution.

EXAMPLE 10

A stability study was performed to measure the stability of the enzyme within a dry patch having 7-FC 4210 stored at room temperature. Release of enzyme after storage comparable to the initial release data reported in the Examples above indicates that the enzyme remains stable during storage. The dry patches were stored for a period of time ranging from 0 to 1 months and the enzyme release was measured at the appropriate time points. Test formulations containing Protease B, 7-FC 4210 base and curing agent silicone and other components were emulsified. The test formulations comprised 36.0000 g dry weight of 7-FC 4210 base silicone, 7.2000 g dry weight of 7-FC 4210 curing agent, 4.08000 g dry weight of DC 225 dimethicone fluid (available from Dow Corning Corp., Midland, Mich.), 4.2006 mg/g Protease B, and 12.2880 g dry weight PVA. The formulations were spread onto a Mylar® sheet using a Blade Applicator (UV Process Supply, Inc., Chicago). The thickness of the applied coating was controlled by adjusting the gap between the blade and the Mylar® sheet. After the coating was allowed to dry or cure completely, 25 mm diameter test discs were cut from the Mylar® sheet. The final dry thickness of the coating was measured using a digital coating thickness gauge (Elcometer, Manchester, UK), and the samples were approximately 100 µm thick. The final dry weight of the test sample disks was also measured so that the enzyme payload is accurately known. The weight and thickness of the Mylar® alone was measured and subtracted from that of the samples on the Mylar® to yield the weight and thickness of the samples alone.

A control comprising Protease B stock solution (50% Sodium formate buffer containing 400 ppm calcium chloride at pH 5.5) in 50% propylene glycol was prepared. The control was stored at room temperature, and the enzymatic activity retained was tested at various time points.

The enzyme release studies were performed using a Hanson (Hanson, Chatsworth, Calif.) dissolution tester equipped with an auto sampling attachment and a small volume dissolution kit. The test samples were fastened to a 3/16" thick glass disc of the same diameter as the sample (25 mm) using rubber cement. The samples were then loaded into the dissolution vessels with the test sample side facing upward. 25 milliters of dissolution buffer (10 mM MES with 10 mM NaCl and 0.005% Tween 80 at pH 5.5) was poured on top of each sample and the stirring paddles along with auto sampler tubes were immediately lowered into the buffer. The dissolution vessel was capped to minimize evaporation and the stirring was started at 50 rpm's. The auto sampler withdrew either a 0.5 ml or 1 ml aliquot at programmed time points and these samples were analyzed for enzyme activity using the SAAPFpNA protease assay referenced above to give an active enzyme concentration in mg/ml. In some cases, total protein was also determined at each time point by measuring the absorbance at 280 nm and applying the appropriate extinction coefficient.

Figure 10:
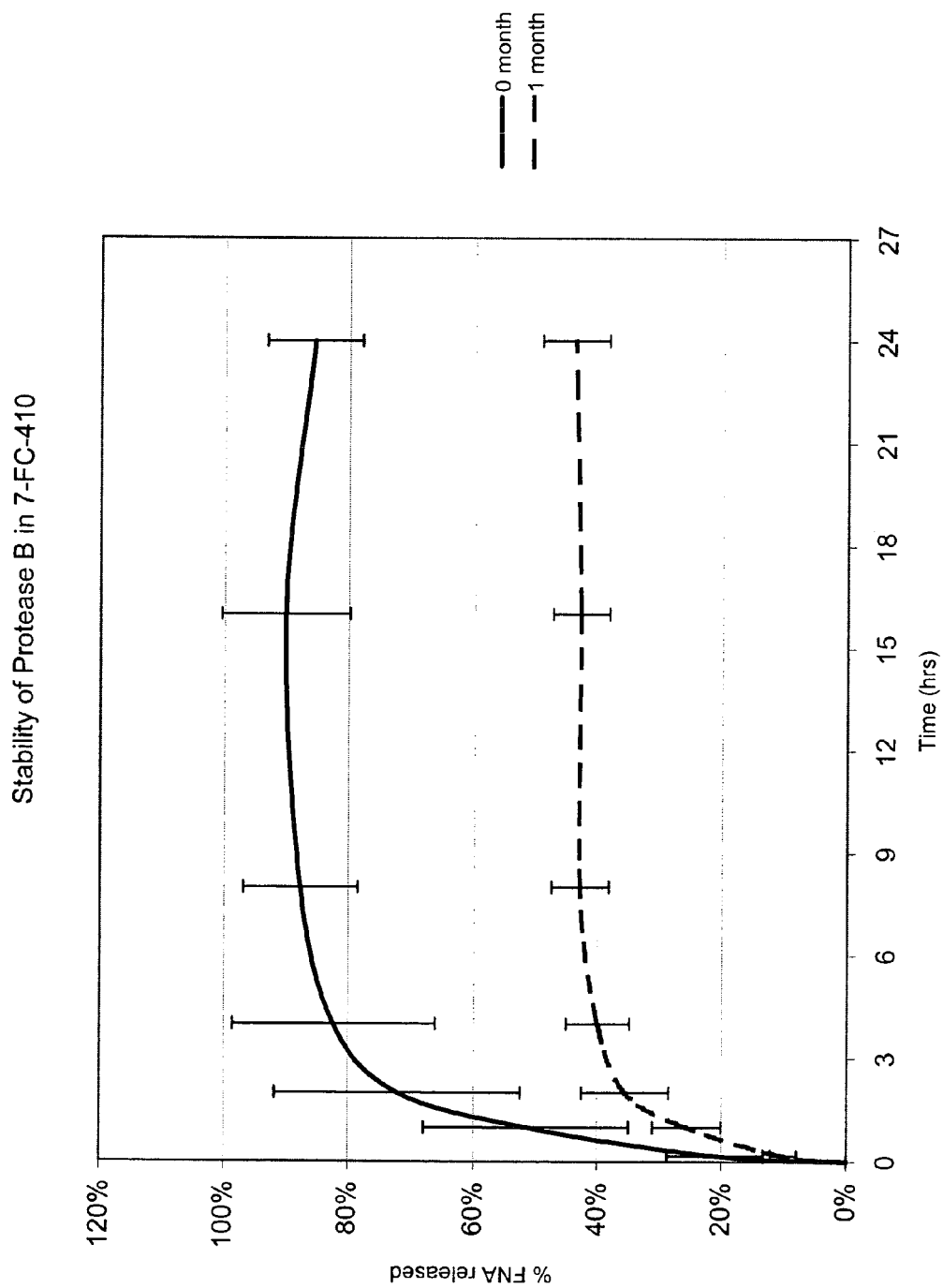
FIG. 10 is a chart showing the stability of protease in preparations in accordance with an embodiment of the present invention.

Referring to FIG. 10, the enzymatic stability of Protease B released from a 7-FC 4210 dry patch stored for 0 and 1 months are illustrated. The data points are from an average of 6 replicates for each time point. The silicone patch provides a stable means of storing and subsequently releasing the enzyme. However, the percentage of Protease B released is less than the percentage of activity retained in the Protease B control solution.

EXAMPLE 11

Discarded eschar was used as an in vitro model for testing the efficacy of enzymes suitable for debridement. Eschar is sloughed off dead tissue from a wound or gangrene. Enzymes provide an alternative to sharp debridement of wounds for patients having limited or no access to facilities for sharp debridement, which utilizes a surgical scalpel or other sharp surgical tool. The discarded eschar was obtained from sharp debridement of foot ulcers occurring in human diabetic patients.

Two large pieces of eschar were obtained on the same day of debridement and divided into two pieces. Each of the two pieces was further subdivided into three sections. A 3×3 fine mesh gauze pad was placed in each of six petrie dishes and the dishes were weighed. A section of eschar was placed on each gauze pad and the petrie dishes were weighed again. The dry weight of the eschar was obtained by subtracting the weight of the petrie dish and gauze from the weight of the petrie dish, gauze and eschar. 20 ml of commercially available phosphate buffered saline (PBS) was added to each petrie dish. Two of the six petrie dishes were controls having only the PBS and an eschar sample from each of the two initial eschar pieces. The PBS in the next two of the six petrie dishes contained 250 µg/20 ml PBS of a proteolytic collagenase enzyme from *Clostridium histolyticum* (Sigma). Each of the PBS solutions in the last two petrie dishes contained 250 µg/20 ml PBS of Protease B subtilisin enzyme from Genencor International, Inc.

The gauze pads with the eschar were then kept immersed in the PBS solutions for 48 hours. After 48 hours, the samples were inspected and a second 20 ml dose of PBS was added to each petrie dish, including an identical 250 µg/20 ml PBS enzyme sample to each of the four enzyme sample petrie dishes. After an additional 48 hours of immersion, the eschar from each petrie dish was transferred to a new 3×3 gauze pad in a new petrie dish. The petrie dishes were weighed.

Table 3 shows the changes in weight of the 6 samples. All samples were heavier at the end of 96 hours presumably because of swelling as the eschar absorbed liquid. The collagenase samples had a lower percent weight gain presumably due to degradation of the eschar. The protease samples also had a lower percent weight gain presumably due to degradation of the eschar.

TABLE 3

Change in Eschar Weight

| sample | Starting weight | End weight | difference | % change |
|---|---|---|---|---|
| Blank 1 | 1.3 g | 1.9 g | 0.6 g | 50% |
| Blank 2 | 0.6 g | 1.0 g | 0.4 g | 66% |
| Collagenase 1 | 1.0 g | 1.4 g | 0.4 g | 40% |
| Collagenase 2 | 2.2 | 2.7 | 0.5 | 23% |
| Protease B 1 | 2.0 | 2.1 | 0.1 | 5% |
| Protease B 2 | 1.5 | 1.7 | 0.2 | 13% |

Visual observations of changes in the structural integrity of the eschar were made at 96 hours and confirm degradation. In samples treated with protease, the eschar became somewhat gelatinous, and in some instances, the eschar completely disintegrated when washed with PBS. The control and collagenase eschar treated samples did not become gelatinous and did not disintegrate when washed with PBS.

It will be obvious to those skilled in the art that various changes may be made without departing from the scope of the invention, which is not to be considered limited to what is described in the specification.

EXAMPLE 12

An in vitro experiment was performed to compare the efficacy of a number of enzymes suitable for debridement. Diabetic foot ulcer eschar and simulated irrigation were used to mimic wound conditions. The experiment was performed in accordance with the following protocol.

Small petri dishes with lids were labeled and weighed. A 2-inch square gauze pad was then added to each petri dish and the dish was reweighed. The diabetic foot ulcer eschar was then separated into visually equal portions using knife or scissors. The samples were test weighed on gauze pads in petri dishes. If the samples were within 10% or 0.1 g of each other, the next step was performed. If the samples were not within 10% or 0.1 g of each other, they were redistributed on the basis of weight until within 10% or 0.1 g.

Then, the eschar on the gauze pads in the petri dishes was weighed. An appropriate volume of enzyme in PBS solution (Dulbecco's Phosphate Buffered Saline, Mediatech, Inc., with 0.002% sodium azide added) was added to the gauze pad to introduce 250 micrograms of enzyme. 10 ml of PBS solution was immediately added. The petri dish was covered and transfered to a sterile hood. Ideally, the 10 ml sodium PBS should be added to the spot where the enzyme was absorbed into the gauze pad to ensure adequate mixing. The petri dishes were allowed to incubate in the sterile hood for 48 hours at room temperature.

After 48 hours, the pad was transferred after draining (touching the pad the side of the petri dish to drain off excess liquid) to a 0.22 micrometer filter in a sterile filter flask with a vacuum attached and open. The pad dried and adhered to the filter. 1 ml of the residual reaction mixture in the petri dish was withdrawn and place in an eppendorf tube for $A_{280}$ analysis at 48 hours.

$A_{280}$ analysis was performed by diluting the sample in the eppendorf tube with PBS solution until the absorbance of the sample was within the linear range of 0.0–2.0 Absorption units. The analysis was performed at 280 nm on an Amersham Bioscience Ultrospec 3100 pro UV/VIS spectrophotometer. The $A_{280}$ analysis provides a measure of whether the enzyme is hydrolyzing the eschar and releasing free amino acids or soluble peptides from the hydrolyzed eschar into the residual reaction mixture.

30 ml of PBS solution was poured over the eschar sample in such a manner that the sample was not washed off the gauze pad. The gauze pad and eschar sample were withdrawn from the filter flask and placed in a second labeled petri dish. The wash was saved in the bottle, and the bottle was covered with screw top. The filter unit was discarded. This wash step simulated irrigation of the wound between after enzyme application.

A second application of enzyme was provided. An appropriate volume of enzyme was added to the gauze pad to introduce 250 micrograms of enzyme. 10 ml of PBS solution was immediately added proximate to the spot where the enzyme was absorbed into the gauze. The petri dish was covered and transfered to a sterile hood. The petri dish was incubated an additional 48 hours.

After 48 hours, the pad was transferred after draining (touching the pad the side of the petri dish to drain off excess liquid) to a 0.22 micrometer filter in a sterile filter flask with a vacuum attached and open. The pad dried and adhered to the filter. 1 ml of the residual reaction mixture in the petri dish was withdrawn and place in an eppendorf tube for $A_{280}$ analysis at 96 hours.

30 ml of PBS solution was poured over the eschar sample in such a manner that the sample was not washed off the gauze pad. The gauze pad and eschar sample were withdrawn from the filter flask and placed in a third labeled and weighed petri dish. The wash was saved in the bottle, and the bottle was covered with screw top. The filter unit was discarded.

The petri dish with the gauze pad was left in a hood overnight and subsequently weighed. The gauze plus eschar weight was calculated. The gauze pad plus eschar was re-weighed after another 24 hours.

The experiment was performed with a blank having only the PBS and an eschar sample. A proteolytic collagenase enzyme from *Clostridium histolyticum* (Sigma) was used. Additionally, Protease B subtilisin enzyme from Genencor International, Inc. was used.

Table 4 shows the weights of the eschar samples before and after the samples were subjected to the enzyme and washes. As can be seen from the table, Protease B appeared to degrade the eschar the most efficiently.

TABLE 4

Change in Eschar Weight

| Sample | Starting weight | End Weight | Difference |
|---|---|---|---|
| Blank | 0.05 g | 0.06 g | 0.01 g |
| Collagenase | 0.07 g | 0.08 g | 0.01 g |
| Protease B | 0.06 g | 0.04 g | −0.02 g |

Table 5 shows the results of the $A_{280}$ analysis at 48 hours and 96 hours of the residual reaction mixture. As can be seen in the table, more free amino acids were present in the Protease B samples. Thus, it appears that Protease B was more effective at degrading the eschar.

TABLE 5

$A_{280}$ Analysis

| Enzyme | Absorbance 48 hours | Difference between Blank | Absorbance 96 Hours | Difference Between Blank |
|---|---|---|---|---|
| Blank | 1.647 | | 0.241 | |
| Collagenase | 1.51 | 0 | 0.360 | 0.119 |
| Protease B | 2.12 | 0.473 | 0.615 | 0.374 |

EXAMPLE 13

An additional experiment was performed as outlined in Example 12. The experiment was performed with a blank having only the PBS and an eschar sample. A proteolytic collagenase enzyme from *Clostridium histolyticum* (Sigma) was used. Additionally, Protease B subtilisin enzyme from Genencor International, Inc was used.

Table 6 shows the results of the $A_{280}$ analysis at 48 hours and 96 hours of the residual reaction mixture. As can be seen in the table, more free amino acids were present in the Protease B samples. Thus, it appears that Protease B was more effective at degrading the eschar.

TABLE 6

$A_{280}$ Analysis

| Enzyme | Absorbance 48 hours | Difference between Blank | Absorbance 96 Hours | Difference Between Blank |
|---|---|---|---|---|
| Blank | 0.505 | | 0.069 | |
| Collagenase | 0.510 | .005 | 0.107 | 0.042 |
| Protease B | 1.135 | 0.630 | 0.182 | 0.113 |

EXAMPLE 14

An additional experiment was performed as outlined in Example 12. The experiment was performed with a blank having only the PBS and an eschar sample. Protease B subtilisin enzyme from Genencor International, Inc was used. Additionally, LG12 a *B. subtilis* protease as described in U.S. Pat. No. 5,677,163, which is incorporated by reference herein, was used.

Table 7 shows the results of the $A_{280}$ analysis at 48 hours and 96 hours of the residual reaction mixture. As can be seen in the table, more free amino acids were present in the LG12 solution. Thus, it appears that LG12 was more effective at degrading the eschar.

TABLE 7

$A_{280}$ Analysis

| Enzyme | Absorbance 48 hours | Difference between Blank | Absorbance 96 Hours | Difference Between Blank |
|---|---|---|---|---|
| Blank | 0.868 | | 0.109 | |
| Collagenase | 0.794 | 0 | 0.122 | 0.013 |
| Protease B | 1.007 | 0.139 | 0.167 | 0.058 |
| LG12 | 1.064 | 0.196 | 0.179 | 0.070 |

EXAMPLE 15

Wafers containing Protease B and 7-5300 silicone were prepared in accordance with Example 5. Additionally a control wafer comprising 7-5300 silicone was prepared. The wafers were placed on a 1.6% casein agar media plate and incubated at 37° C. for 1 hour. The wafers containing the protease B enzyme hydrolyzed the skim milk to give clearing of the agar. The control wafer did not dissolve the skim milk to give clearing.

EXAMPLE 16

A patch containing Protease B and PSA 7-4402 silicone were prepared in accordance with Example 8. The patch was stored for 13 months at room temperature. The patch was placed on a 1.6% casein agar media plate and incubated at 37° C. for 1 hour. The patch hydrolyzed the skim milk to give a small amount of clearing of the agar. The plate was then incubated overnight at 37° C., and the patch further hydrolyzed the skim milk to give about the same amount of clearing as the 7-5300 Protease B patches in Example 15.

What is claimed is:

1. A method of removing necrotic tissue from the skin of a patient in need thereof comprising:

providing a topical preparation, wherein said topical preparation comprises an internal phase and an external phase, wherein said internal phase is dispersed within said external phase, wherein said internal phase comprises at least one hydrophilic carrier, at least one hydrophilic component containing water, and at least one active agent comprising an enzyme, and wherein said external phase comprises a silicone matrix; and contacting said topical preparation with the necrotic tissue on the skin of said patient, such that said active agent is released from said silicone matrix onto said necrotic tissue on the skin, wherein said enzyme removes said necrotic tissues upon said release.

2. The method as claimed in claim 1 wherein said silicone matrix is selected to have a cross-link density suitable for providing a desired rate of active agent release from said silicone matrix.

3. The method as claimed in claim 1 wherein said hydrophilic component is selected such that said active agent is released from said silicone matrix at a desired rate.

4. The method as claimed in claim 1 wherein said topical preparation comprises a patch having a thickness, and wherein said thickness of said patch is selected such that said active agent is released from said silicone matrix at a desired rate.

5. The method as claimed in claim 1 wherein said topical preparation has an occlusivity to air, and wherein said occlusivity to air of said topical preparation is selected such that said active agent is released from said silicone matrix at a desired rate.

6. The method as claimed in claim 1 wherein:

said topical preparation has an occlusivity to fluid;

said occlusivity to fluid promotes a moist environment that allows swelling of necrotic tissues covered by said topical preparation such that said necrotic tissue becomes swollen; and said active agent is released from said silicone matrix selectively removes said swollen necrotic tissues.

7. The method as claimed in claim 1 wherein said at least one hydrophilic carrier comprises polypropylene glycol.

8. The method as claimed in claim 1 wherein said at least one active agent comprises at least one hydrolase enzyme.

9. The method as claimed in claim 8 wherein said hydrolase enzyme is selected from lipases and proteases.

10. The method as claimed in claim 9 wherein said protease comprises LG12.

11. A method of providing an active agent topically to remove necrotic tissue, comprising:

providing a first topical preparation, wherein said first topical preparation comprises an internal phase and an external phase; wherein:

said internal phase is dispersed within said external phase; said internal phase comprises at least one hydrophilic carrier and at least one active agent comprising a protease enzyme; and said external phase comprises a silicone matrix;

providing a second topical preparation comprising an internal phase and external phase, wherein:

said internal phase is dispersed within said external phase; said internal phase comprises at least one hydrophilic carrier and at least one second active agent comprising a protease inhibitor that inhibits said active agent selected to remove necrotic tissue;

said external phase comprises a silicone matrix comprising a silicone adhesive;

placing said topical preparation in contact with a wound having necrotic tissue on the skin of a patient such that said active agent is released from said silicone matrix topically onto said wound; and placing said second topical preparation on said skin of said patient around said wound, said second topical preparation adhering said first topical preparation over said wound, wherein said skin of said patient around said wound is protected from said active agent selected to remove said necrotic tissue;

wherein said active agent removes necrotic tissue.

12. The method as claimed in claim 11 wherein said protease enzyme active agent comprises LG12.

13. A method of removing necrotic tissues from the skin of a patient in need thereof comprising:

providing a topical preparation, wherein said topical preparation comprises an internal phase and an external phase, wherein said internal phase is dispersed within said external phase, wherein said internal phase comprises at least one hydrophilic carrier, at least one hydrophilic component containing water, and at least one active agent comprising LG12 protease, and wherein said external phase comprises a silicone matrix; and contacting said topical preparation with the necrotic tissues on the skin of said patient, such that said LG12 protease enzyme is released from said silicone matrix onto said necrotic tissues on the skin, wherein said LG12 protease enzyme removes said necrotic tissues upon said release.

14. The method as claimed in claim 13 further comprising:

providing a second topical preparation comprising an internal phase and external phase, wherein said internal phase is dispersed within said external phase, wherein said internal phase comprises at least one hydrophilic carrier, at least one hydrophilic component containing water, and an LG12 protease enzyme inhibitor, and wherein said external phase comprises a silicone matrix; and wherein said silicone matrix comprises a silicone adhesive; and placing said second topical preparation on said skin of said patient around a wound comprising necrotic tissues on said skin and adhering said first topical preparation over said wound by contacting said first topical preparation to said second topical preparation, such that the skin around the wound is protected from said LG12 protease enzyme.

15. A method of cleansing a wound on the skin of a patient in need thereof comprising:

providing a topical preparation, wherein said topical preparation comprises an internal phase and an external phase, wherein said internal phase is dispersed within said external phase, wherein said internal phase comprises at least one hydrophilic carrier, at least one hydrophilic component containing water, and at least one active agent comprising LG12 protease enzyme, and wherein said external phase comprises a silicone matrix; and contacting said topical preparation with the wound on the skin of said patient, such that said LG12 protease enzyme is released from said silicone matrix onto said wound on the skin, wherein said LG12 protease enzyme cleanses said wound upon said release.

16. The method as claimed in claim 15 further comprising:
providing a second topical preparation comprising an internal phase and external phase,
wherein said internal phase is dispersed within said external phase,
wherein said internal phase comprises at least one hydrophilic carrier, at least one hydrophilic component containing water, and an LG12 protease enzyme inhibitor, and
wherein said external phase comprises a silicone matrix; and
wherein said silicone matrix comprises a silicone adhesive; and
placing said second topical preparation on said skin of said patient around a wound comprising necrotic tissues on said skin and adhering said first topical preparation over said wound by contacting said first topical preparation to said second topical preparation, such that the skin around the wound is protected from said LG12 protease enzyme.

17. A method of cleansing a wound on the skin of a patient in need thereof comprising:
providing a topical preparation, wherein said topical preparation comprises an internal phase and an external phase,
wherein said internal phase is dispersed within said external phase,
wherein said internal phase comprises at least one hydrophilic carrier, at least one hydrophilic component containing water, and at least one active agent comprising an enzyme, and wherein said external phase comprises a silicone matrix; and contacting said topical preparation with the wound on the skin of said patient, such that said active agent is released from said silicone matrix onto said wound on the skin, wherein said enzyme cleanses said wound upon said release.

18. The method as claimed in claim 17 wherein said silicone matrix is selected to have a cross-link density suitable for providing a desired rate of active agent release from said silicone matrix.

19. The method as claimed in claim 17 wherein said hydrophilic component is selected such that said active agent is released from said silicone matrix at a desired rate.

20. The method as claimed in claim 17 wherein said topical preparation comprises a patch having a thickness, and wherein said thickness of said patch is selected such that said active agent is released from said silicone matrix at a desired rate.

21. The method as claimed in claim 17 wherein said topical preparation has an occlusivity to air, and wherein said occlusivity to air of said topical preparation is selected such that said active agent is released from said silicone matrix at a desired rate.

22. The method as claimed in claim 17 wherein said at least one hydrophilic carrier comprises polypropylene glycol.

23. The method as claimed in claim 17 wherein said at least one active agent comprises at least one hydrolase enzyme.

24. The method as claimed in claim 23 wherein said hydrolase enzyme is selected from lipases and proteases.

25. The method as claimed in claim 24 wherein said protease comprises LG12.

* * * * *